United States Patent
Ju et al.

(10) Patent No.: US 12,163,157 B2
(45) Date of Patent: Dec. 10, 2024

(54) METHOD FOR PREPARING PELLETS OF CHONDROCYTES FROM HUMAN INDUCED PLURIPOTENT STEM CELLS, AND USE THEREOF

(71) Applicant: YiPCELL Inc., Seoul (KR)

(72) Inventors: Ji Hyeon Ju, Seoul (KR); Yoo Jun Nam, Bucheon-si (KR); Ye Ri Rim, Seoul (KR)

(73) Assignee: YiPCELL Inc., Seoul (KR)

( * ) Notice: Subject to any disclaimer, the term of this patent is extended or adjusted under 35 U.S.C. 154(b) by 921 days.

(21) Appl. No.: 17/253,742

(22) PCT Filed: Jun. 25, 2019

(86) PCT No.: PCT/KR2019/007633
§ 371 (c)(1),
(2) Date: Dec. 18, 2020

(87) PCT Pub. No.: WO2020/004893
PCT Pub. Date: Jan. 2, 2020

(65) Prior Publication Data
US 2021/0261920 A1    Aug. 26, 2021

(30) Foreign Application Priority Data
Jun. 25, 2018 (KR) .......... 10-2018-0072875

(51) Int. Cl.
*C12N 5/00*    (2006.01)
*A61K 31/70*    (2006.01)
(Continued)

(52) U.S. Cl.
CPC .......... *C12N 5/0655* (2013.01); *A61K 31/728* (2013.01); *A61K 35/32* (2013.01);
(Continued)

(58) Field of Classification Search
CPC ............................ C12N 5/0655; A61K 31/728
See application file for complete search history.

(56) References Cited

U.S. PATENT DOCUMENTS 9,707,190 B2 * 7/2017 Segal ................. A61K 31/728
10,100,283 B2   10/2018 Tsumaki
(Continued)

FOREIGN PATENT DOCUMENTS

KR   20160068982 A   6/2016
KR   20180085699 A   7/2018

OTHER PUBLICATIONS

Li et al. Impact of vitronectin concentration and surface properties on the stable propagation of human embryonic stem cells. Biointerphases 5: FA 132-142. (Year: 2010).*
(Continued)

*Primary Examiner* — Arthur S Leonard
*Assistant Examiner* — Keenan A Bates
(74) *Attorney, Agent, or Firm* — Rothwell, Figg, Ernst & Manbeck, P.C.

(57) ABSTRACT

A method for preparing chondrocyte pellets including: (a) culturing human induced pluripotent stem cells so as to form and obtain embryoid bodies; (b) inducing the embryonic bodies obtained in step (a) to become outgrowth cells and isolating same; and (c) culturing the outgrowth cells isolated in step (b) in a pellet form. A pharmaceutical composition including the chondrocyte pellets prepared by the preparation method; or a method for preventing or treating arthritis, including administering the chondrocyte pellets prepared by the method to an arthritis patient. Chondrocyte pellets of the present invention have a remarkably high rate of differentiation into chondrocytes, uniform size, and a homogeneous differentiation degree, and a pharmaceutical composition, including the pellets, has excellent cartilage regeneration effects at the site of cartilage damage, and is in injectable (Continued)

form, which does not require surgery, such that pain is relieved and a continuous arthritis treatment is provided.

6 Claims, 12 Drawing Sheets

(51) Int. Cl.
  *A61K 31/728* (2006.01)
  *A61K 35/32* (2015.01)
  *C12N 5/077* (2010.01)
(52) U.S. Cl.
  CPC ...... *C12N 2500/99* (2013.01); *C12N 2501/15* (2013.01); *C12N 2501/155* (2013.01)

(56) References Cited

U.S. PATENT DOCUMENTS

| | | | |
|---|---|---|---|
| 11,624,056 B2 * | 4/2023 | Ju ..................... | C12N 5/0655 424/93.7 |
| 2014/0271616 A1 * | 9/2014 | Nejadnik ............. | C12N 5/0662 424/130.1 |

OTHER PUBLICATIONS

Babur et al. The Interplay between Chondrocyte Redifferentiation Pellet Size and Oxygen Concentration. PLOS One 8: 1-12. (Year: 2013).*
Huang et al. Pellet coculture of osteoarthritic chondrocytes and infrapatellar fat pad-derived mesenchymal stem cells with chitosan/hyaluronic acid nanoparticles. Stem Cell Research & Therapy 8: 1-12. (Year: 2017).*
Murphy et al. The Potency of Induced Pluripotent Stem Cells in Cartilage Regeneration and Osteoarthritis Treatment. Springer International Cell Biology and Translational Medicine 1: Chapter 4: 55-68. Accessible Dec. 2017. (Year: 2018).*
Pereira et al. Emerging Concepts in Treating Cartilage, Osteochondral Defects, and Osteoarthritis of the Knee and Ankle. Springer International Osteochondral Tissue Engineering Chapter 2: 25-62. Jan. 2018. (Year: 2018).*
Pereira et al. Hyaluronic Acid. Springer International Osteochondral Tissue Engineering Chapter 6: 137-154. Jan. 2018. (Year: 2018).*
Jimenez et al. Osteoarthritis: Trauma vs Disease. Springer International Osteochondral Tissue Engineering Chapter 3: 63-85. Jan. 2018. (Year: 2018).*
Gibson et al. Regeneration of Articular Cartilage by Human ESC-Derived Mesenchymal Progenitors Treated Sequentially with BMP-2 and Wnt5a. Stem Cells Translational Medicine 6: 40-50. (Year: 2017).*
G Force Calculator—RCF to RPM. Millipore Sigma. https://www.sigmaaldrich.com/US/en/support/calculators-and-apps/g-force-calculator. Accessed Sep. 19, 2023. (Year: 2023).*
Huang et al. Study of differential properties of fibrochondrocytes and hyaline chondrocytes in growing rabbits. British Journal of Oral and Maxillofacial Surgery 53: 187-193. (Year: 2015).*
Nam et al. Cord blood cell-derived iPSCs as a new candidate for chondrogenic differentiation and cartilage regeneration Stem Cell Research & Therapy 8: 1-13. Jan. 2017 (Year: 2017).*
Li et al., "Reprogramming of blood cells into induced pluripotent stem cells as a new cell source for cartilage repair", Stem Cell Research & Therapy (2016) 7:31, 11 pgs.
Messana et al., "Size of the embryoid body influences chondrogenesis of mouse embryonic stem cells". J Tissue Eng Regen Med 2008; 2: 499-506.
Nam et al., "Cord blood cell-derived iPSCs as a new candidate for chondrogenic differentiation and cartilage regeneration", Stem Cell Research & Therapy (2017) 8:16, 13 pgs.
Rim et al., "Different Chondrogenic Potential among Human Induced Pluripotent Stem Cells from Diverse Origin Primary Cells", Stem Cells International, 2018, Article ID 9432616, 13 pgs.
Shen et al., "BMP-2 Enhances TGF-b3-Mediated Chondrogenic Differentiation of Human Bone Marrow Multipotent Mesenchymal Stromal Cells in Alginate Bead Culture", Tissue Engineering: Part A vol. 15, No. 6, 2009, 10 pgs.
International Search Report cited in PCT/KR2019/007633 dated Oct. 11, 2019, 4 pages.
Nam et al: "Current Therapeutic Strategies for Stem Cell-Based Cartilage Regeneration", Stem Cells International, vol. 2018, Mar. 25, 2018, Article ID 8490489, 20 pgs., XP055841512.
Extended European Search Report issued in EP19825602.6 dated Mar. 24, 2022, 8 pgs.
Nam, Yoojun et al., "Chondrogenic Pellet Formation from Cord Blood-derived Induced Pluripotent Stem Cells", Journal of Visualized Experiments Jun. 2017 | 124 | e55988 | 8 pgs.

* cited by examiner

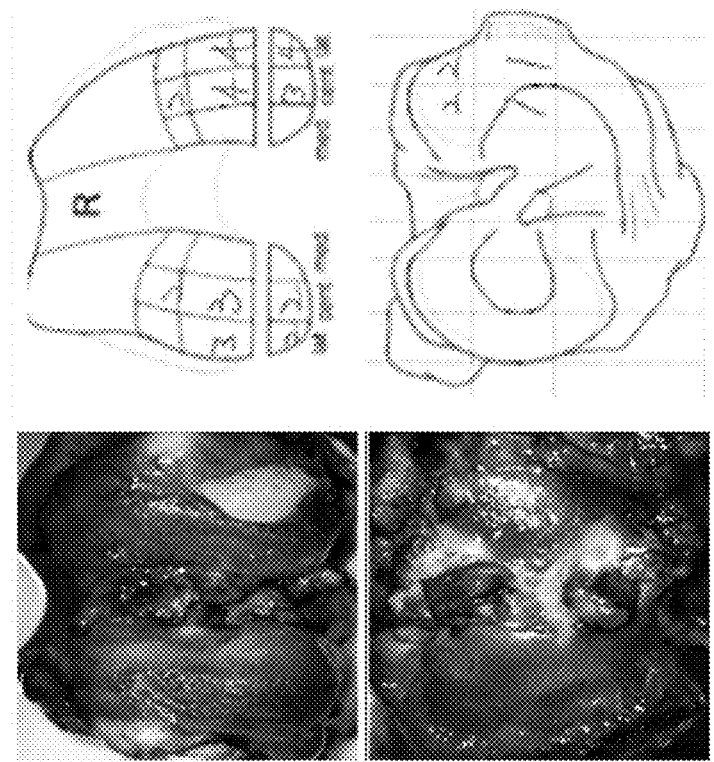
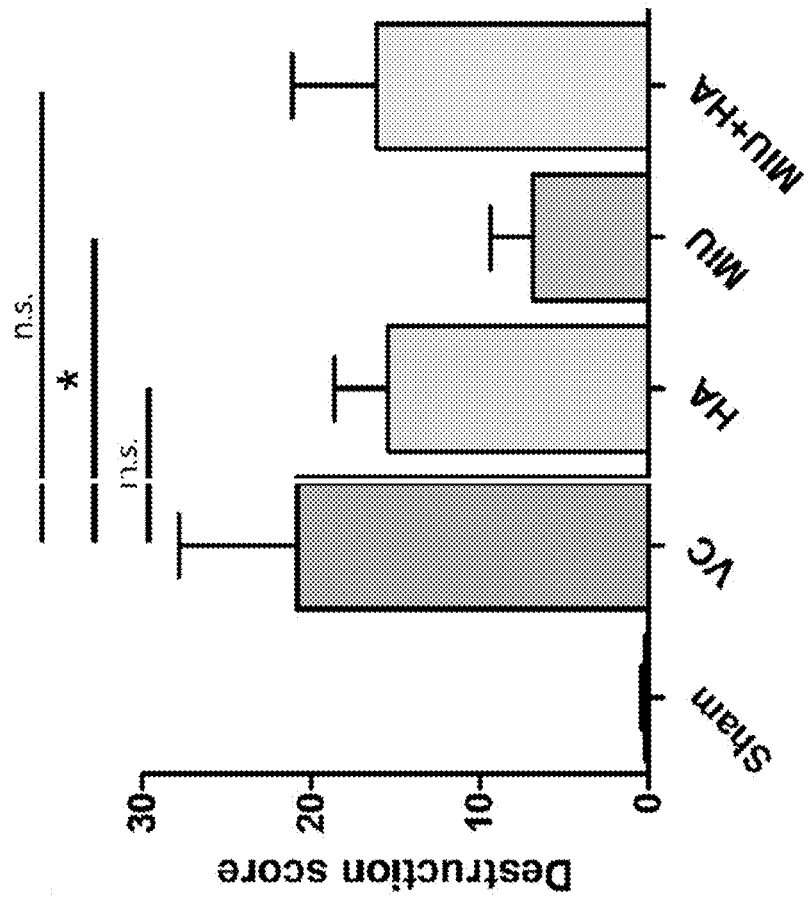
FIG. 12B
FIG. 12A
FIGS. 12A-12B

METHOD FOR PREPARING PELLETS OF CHONDROCYTES FROM HUMAN INDUCED PLURIPOTENT STEM CELLS, AND USE THEREOF

This application is a 35 U.S.C. 371 National Phase Entry Application from PCT/KR2019/007633, filed Jun. 25, 2019, which claims priority to and the benefit of Korean Patent Application No. 10-2018-0072875, filed on Jun. 25, 2018, the disclosure of which are incorporated herein by reference in their entirety.

FIELD OF THE INVENTION

The present invention relates to a method of preparing a chondrocyte pellet, which includes: (a) culturing human induced pluripotent stem cells to form and obtain an embryoid body; (b) inducing the embryoid body obtained in Step (a) into outgrowth cells and isolating the same; and (c) culturing the outgrowth cells isolated in Step (b) in a pellet form.

The present invention also relates to a pharmaceutical composition for use in arthritis treatment, which includes the chondrocyte pellets prepared by the above-described method.

The present invention relates to a method of preventing or treating arthritis, which includes administering the chondrocyte pellets prepared by the above method to an arthritis patient.

BACKGROUND

Cartilage is bone tissue consisting of chondrocytes and the matrix of cartilage, and generally refers to tissue that is a part of joint. Due to high elasticity and a very low coefficient of friction, cartilage serves as a cushion that prevents the friction of bone ends, and thus helps a joint to move with almost no friction. In addition, cartilage plays a role in constituting a region which requires elasticity such as respiratory organs or auricles, or resistance to pressure, such as costal cartilage or pubic symphysis cartilage.

Articular cartilage is elastic white tissue, which surrounds the end of a bone and protects the bone from friction. Articular cartilage is formed of the extracellular matrix consisting of various types of collagens, proteoglycans and flexible fibers, and chondrocytes, which are specifically differentiated cells to be distributed in the cartilage matrix.

Chondrocytes serve to make and maintain articular cartilage by producing a composition of the extracellular matrix. Although cell division occurs in chondroblasts, once growth stops, chondrocytes no longer divide in a normal environment. In addition, since chondrocytes are confined in a small area called a lacuna, once cartilage is damaged, the migration and recovery of chondrocytes are difficult. Moreover, since cartilage is avascular tissue, there are no blood vessels for the supply of nutrients, and thus the migration of stem cells is hindered and the regenerative capacity of tissue is reduced. These characteristics mean that it is almost impossible that once-damaged cartilage is naturally repaired. For this reason, it is important to produce functional chondrocytes that can produce the extracellular matrix in vitro, or obtain fully grown cartilage for implantation.

To treat damaged cartilage tissue, drug therapy (painkillers, steroids, nonsteroidal anti-inflammatory drugs, etc.), cartilage protective agents (hyaluronic acid, glucosamine, chondroitin, etc.), or surgical treatment (arthroscopy, high tibial osteotomy, unicondylar knee arthroplasty, total knee arthroplasty, bone marrow stimulation, osteochondral graft, etc.) may be used.

However, drug therapy only has an effect of non-specifically relieving pain or an inflammatory response itself, and a cartilage protective agent may serve to temporarily protect a joint by simply supplying nutrition to chondrocytes or softening impact.

In addition, various orthopedic surgeries are performed clinically, and typically include bone marrow stimulation and osteochondral graft. Bone marrow stimulation is a method in which a damaged subchondral bone is exposed to fill cartilage damage with blood clots containing bone marrow-derived stem cells, and this method is a relatively simple surgery, but has a disadvantage of regeneration of fibrotic cartilage, rather than hyaline cartilage, after surgery. Osteochondral graft is a therapeutic method of transplanting bone-cartilage connective tissue that has been previously taken from a patient's own cartilage tissue in a region which is subjected to less load by his/her body weight into a cartilage damage site, and this method has a disadvantage that it cannot be used when a damage site is large.

To overcome the shortcomings of these surgical treatment techniques, much research on cell therapeutic agents providing therapeutic cells from outside is being conducted. The first commercialized technique is autologous chondrocytes implantation, which is a technique of detaching a little bit of healthy cartilage from a region of a patient's cartilage tissue, which is subjected to less load by body weight, isolating chondrocytes therefrom, and then injecting them again into the damage site after in vitro culture, and has disadvantages that there is a hassle of undergoing two surgeries, cartilage in a healthy region is damaged, due to a lower number of obtained chondrocytes, the cells should be cultured for a certain period, dedifferentiation in which the phenotype of chondrocytes is not maintained occurs during the culture period, cell viability after implantation is reduced, and the implanted chondrocytes are not uniform and are localized in a specific region due to gravity so that they are not well distributed.

To overcome the shortcomings in in vivo distribution and differentiation of a cell therapeutic agent, technology of delivering cells using various forms of biomaterials as scaffolds has been used, and moreover, tissue-engineering technology of in vitro manufacturing tissue-engineered cartilage having a three-dimensional structure is being developed.

In the manufacture of tissue-engineered cartilage, a scaffold provides a three-dimensional system to chondrocytes such that the phenotype of the chondrocytes is maintained and production of hyaline cartilage extracellular matrix is promoted. In addition, the scaffold transfers the cells to a cartilage damage site and imparts a physical support to an implanted site to protect the cells from an applied force. Currently used scaffolds for cell transfer to the implanted site have various forms such as sponge, gel, fiber and microbeads, and are usually manufactured using natural or synthetic biomaterials. When a scaffold is used, it is highly effective for implantation itself and can allow cells to be uniformly distributed in the implanted site, but when the cells are proliferated or the extracellular matrix is secreted in the scaffold, the scaffold itself can rather limit space. Particularly, a hydrogel-type scaffold has poor supply of oxygen and nutrients so that cell viability and cartilage differentiation are reduced; a membrane-type scaffold cannot form three-dimensional cartilage tissue; and when a three-dimensional sponge or mesh-type scaffold is used, manufactured artificial cartilage has low bonding strength to host tissue so that it is difficult to regenerate cartilage. In addition, all scaffolds are degradable, and natural biomaterials with a high degradation rate have a high possibility of cells being lost while degradation occurs, in terms of clinical application, xenogeneic and allogeneic natural materials may trigger immune responses, and since synthetic materials sometimes have harmful degradation products, they are not free from safety issues.

Research on a method of manufacturing artificial cartilage tissue having a three-dimensional structure without a scaffold has been continuously conducted, and since this method forms tissue depending on only cells and their ability to synthesize the extracellular matrix, it is difficult to form tissue suitable for a damage size requiring implantation, and thus this method is very limited in direct clinical application.

In addition, since the shape and depth of cartilage damage are not uniform, when artificial cartilage having a three-dimensional structure, which has been manufactured in a laboratory, is larger than the damage site, an implant needs to be trimmed to the shape of the damage, whereas when a cartilage implant is smaller than the damage site, it has to be implanted according to a damaged shape by being pieced together like a mosaic. Currently developed tissue-engineering cartilage products are implanted by the above-cited method, but cannot match the thickness of the damage. For this reason, when the implant is higher or lower than peripheral tissues of articular cartilage, additional damage to the implant or normal cartilage around the same is caused by abnormal weight bearing.

As a method of forming a scaffold-free small cartilage structure, there is a method of naturally inducing cell aggregation. A cell aggregate referred to as an aggregation pattern can be formed using a rotation technique, and according to dynamic culture of cells in a suspended state, a cell aggregate is naturally formed by an intercellular action.

For example, in a spheroid system for manufacturing a three-dimensional cell aggregate by manipulating cells on a non-adhesive plastic surface, cells from a three-dimensional cell aggregate, and their own extracellular matrix similar to the matrix of hyaline cartilage is naturally produced. However, since this culture method cannot regulate the number of cells forming one cell aggregate and fusion between the formed chondrogenic tissues may occur, there will be variations in the size of chondrogenic tissue and the degree of cartilage differentiation, and thus such a cell aggregate cannot be standardized as a cell therapeutic agent.

As another example, there is a micromass/chondrosphere culture method using an adhesive culture dish, in which a high-concentration suspension of cells having cartilage differentiation ability is dropped on an adhesive culture dish and maintained in a 37° C. incubator, thereby aggregating the cells within several hours to several days, and the cell aggregate is suspended in a culture medium, followed by three-dimensional culture in a non-adhesive culture dish or under a dynamic culture condition. This method has an advantage of regulating the number of cells forming chondrogenic tissue, but due to a difference in ability of naturally forming a cell aggregate according to the state of cells, the method cannot ensure stable acquirement of uniform chondrogenic tissues. In addition, before the extracellular matrix becomes hard, when the cell aggregates are cultured at the same time, there may be fusion between the formed chondrogenic tissues.

To equalize the number of cells naturally forming a cell aggregate, research using a microwell was also performed. In three-dimensional culture of hepatocytes, since a large hepatosphere has necrosis in the core thereof, the development of a three-dimensional culture system that can form a large amount of uniform hepatospheres in a desired size was required. Micromolding techniques or techniques using a concave micromold having a diameter of 300 to 500 μm manufactured based on a thin poly-dimethylpolysiloxane (PDMS) membrane were suggested. When spheroids were formed by culturing hepatocytes in a flat PDMS-based, cylindrical or concave microwell, the size and shape of a sphere formed in a concave microwell were uniform, the size was perfectly regulated by the diameter of the concave microwell, and the cells cultured in the concave microwell rapidly form a sphere on a cylindrical microwell or flat surface and are easily recovered, which becomes a great advantage in obtaining a stable sphere. The method of manufacturing micro-tissue using a micromold is evaluated in various cells with a commercialized mold, but since it is also a method of inducing natural cell aggregation, it cannot ensure stable acquirement of uniform chondrogenic tissue. In addition, since the formed cell aggregate is very small, it has poor physical strength and is difficult to handle, and therefore, it is limited in use as a three-dimensional chondrocyte-based therapeutic agent.

Meanwhile, among the methods of forming a small cartilage structure without a scaffold, pellet culture is a method of centrifuging a relatively small number of cells to achieve cell aggregation, and artificially forming an ultra-high-density culture system of cells from the initial step of three-dimensional culture. The pellet forming process is simple and easily reproducible, and cells having cartilage-forming ability synthesize and secrete a chondrogenic extracellular matrix under this system, thereby forming chondrogenic tissue. The pellet culture is the most widely used method of evaluating the ability of differentiating stem cells into chondrocytes, and also has been used for evaluating the effect of foreign factors on chondrocytes. However, the evaluation of the availability of the cartilage structure formed by pellet culture as a cell therapeutic agent was not performed. Although the pellet system is a useful method for forming high-quality chondrogenic tissue, it has been considered that it is difficult to be applied in regeneration of a cartilage damage site because of difficulty in forming a pellet with a sufficient size. In addition, general pellet culture had a disadvantage that there is difficulty in mass culture because a method of putting a cell suspension into a capped tube (conical tube, storage tube, microcentrifuge tube, etc.), centrifuging, and performing three-dimensional culture to form one pellet per tube was used.

Accordingly, when chondrocytes are prepared in an injectable form by pellet culture, the problem of low reproducibility of chondrocytes may be overcome, there may be no death of inner cells caused by perfusion during culture, and by administering several pellets of chondrocytes to a damage site, they can be applied regardless of the shape and thickness of the cartilage damage site. In addition, since chondrocytes are prepared in an injectable form, incision of the cartilage damage site is not required. However, to develop a therapeutic agent, technology of forming a repeatedly reproducible and uniform chondrogenic tissue is needed, and to be used for a wide damage site, a mass-culture system that can manufacture a considerably large amount of chondrogenic tissue is required.

To overcome this, as development of artificial cell culture techniques, a method of artificially culturing chondrocytes for implantation from multipotent stem cells or mesenchymal stem cells was reported. Recently, techniques for implant treatment on a cartilage damage site by culturing allogeneic cord blood-derived mesenchymal stem cells have been commercialized (Korean Patent No. 10-0494265). Since mesenchymal stem cells are relatively easily obtained, they are already widely used as a composition for cell therapy for various diseases such as rheumatoid arthritis and osteoarthritis. However, because of a low differentiation rate and an unstable phenotype, the mesenchymal stem cells are most likely to have undesirable differentiation or transformation during differentiation, and therefore, a large amount of mesenchymal stem cells has to be collected from a patient. In addition, it has been reported that the mesenchymal stem cells lose their intrinsic characteristics after 3 to 4 days ex vivo, and the production and differentiation ability of the mesenchymal stem cells differ according to the age of a patient and the status of a disease. In addition, due to the expression of hypertrophy-related genes after in vivo implantation, the mesenchymal stem cells cause apoptosis and vascular penetration, resulting in calcification of chondrocytes. Therefore, a new cell source is required for culturing chondrocytes ex vivo.

When cartilage tissue forming a joint is damaged, arthritis with swelling, fever and pain is triggered. Arthritis occurs regardless of race, and is divided into approximately 100 types according to their causes. Among these types, the most common type is osteoarthritis, which is a degenerative joint disease usually caused by aging, followed by rheumatoid arthritis and psoriatic arthritis, which are autoimmune diseases, and septic arthritis caused by infection. Particularly, degenerative arthritis is a representative disease of older people, which is generally caused by the aging of joints, but is also a frequently occurring disease in younger people because it occurs due to the action of a combination of several factors such as genetic factors, nutrient imbalance, insufficient exercise, actions or wrong posture putting strain on the joints, such as strenuous exercise, injury or excessive work, and overload caused by obesity. Like this, arthritis is a disease with very high incidence in a wide range of age groups, and due to the fact that once-damaged tissue is not naturally regenerated or repaired, it becomes a cause of limiting the social activity of a patient and reducing his/her quality of life for a long time.

Currently used agents for arthritis are mostly therapeutic agents requiring surgery, and these agents take a long time for repair or do not have distinct cartilage regeneration efficacy.

Pluripotent stem cells refer to stem cells having pluripotency, which can differentiate into all three types of germ layer constituting the living body and then into all cells or organ tissues of the human body, and generally denote embryonic stem cells. Since human embryonic stem cells are produced from an embryo that is able to develop into a human, they have many ethical problems, but are known to exhibit excellent cell proliferation and differentiation, compared with adult stem cells. Human induced pluripotent stem cells (hiPSCs) have been highlighted as an alternative cell source for regenerative medicine. The hiPSCs may be obtained from various cells with a combination of a compound or a genetic factor, and since there are no ethical problems with embryonic stem cells, the hiPSCs have high applicability. For this reason, the discovery of hiPSCs has provided a new strategy in drug screening and therapeutic research for various diseases.

Unlike mesenchymal stem cells, since hiPSCs have excellent ability of differentiating into target cells including chondrocytes, they can be a cell source to replace damaged tissue that is limited in regenerative capacity, for example, articular cartilage. In addition, since hiPSCs have unlimited proliferation ability, they are considered an alternative source that can be used as a cell source for chondrocyte culture suitable for mass production under a suitable culture environment.

A disadvantage that a culture technique for maintaining and proliferating undifferentiated hiPSCs is very complicated, and it takes a considerably long time to fully differentiate human induced pluripotent stem cells into specific cells has become one of the biggest impediments to the development of related techniques including a differentiation-inducing technique. At the current level, a differentiation-inducing method via manufacture of an embryoid body has been mostly used in a universal differentiation induction technique using hiPSCs. That is, for cell-specific differentiation culture of human induced pluripotent stem cells in vitro, a step of spontaneously aggregating cells into a spherical form called an embryoid body through suspension culture must be determined in advance, and the embryoid body is used as a common and important medium for inducing lineage-specific differentiation.

Various methods of preparing chondrocytes from hiPSCs have been reported, but to differentiate chondrocytes from human induced pluripotent stem cells, a required period increases, unpacking of chondrocyte pellets occurs in the cultured pellets, chondrocytes that are not fully mature are obtained, or hiPSCs differentiate into non-chondrocytes as well as the chondrocytes, and there is a limit that there is diversity in the degree of differentiation for each chondrocyte.

SUMMARY OF THE INVENTION

Therefore, as a result of earnest attempts to ensure reproducibility of chondrocytes, solve problems of mass production, considerably increase the differentiation rate into chondrocytes, and develop chondrocyte pellets which have a uniform size and a uniform degree of differentiation, the inventors prepared pellets containing outgrowth cells induced by adherent culture of an embryoid body obtained from human induced pluripotent stem cells (hiPSCs) and injected them into a cartilage damage site with a syringe, confirming an excellent effect of regenerating cartilage, and thus the present invention was completed.

The present invention is directed to providing a method of preparing pellets which have a high differentiation rate into chondrocytes from hiPSCs, a uniform size and a uniform degree of differentiation.

The present invention is directed to providing a pharmaceutical composition which has an excellent effect of regenerating cartilage and is prepared in an injectable form to be used for arthritis treatment, not requiring surgery, and a method of preventing or treating arthritis.

To attain the above problems, the present invention provides a method of preparing a chondrocyte pellet, which includes: (a) culturing human induced pluripotent stem cells (hiPSCs) to form and obtain an embryoid body; (b) inducing the embryoid body obtained in Step (a) into outgrowth cells and isolating the same; and (c) culturing the outgrowth cells isolated in Step (b) in a pellet form.

According to one exemplary embodiment of the present invention, the hiPSCs in Step (a) may be derived from cord blood mononuclear cells.

According to one exemplary embodiment of the present invention, the culture in Step (a) may be adherent culture.

According to one exemplary embodiment of the present invention, the induction in Step (b) may be performed on a gelatin-coated plate.

According to one exemplary embodiment of the present invention, Step (c) may be to centrifuge the isolated outgrowth cells and culture the cells in a pellet form.

According to one exemplary embodiment of the present invention, the centrifugation may be performed at a speed of 1,100 to 2,500 rpm.

According to one exemplary embodiment of the present invention, in Step (c), 95 to 100% of the isolated outgrowth cells may be formed into a chondrocyte pellet.

According to one exemplary embodiment of the present invention, the culture of Step (c) may be performed in a serum-free medium containing a human bone morphogenetic protein (BMP) and transforming growth factor-beta (TGF-β).

According to one exemplary embodiment of the present invention, the chondrocyte pellet may contain 200 to 5,000 of the outgrowth cells of Step (b).

According to one exemplary embodiment of the present invention, the chondrocyte pellet may differentiate into hyaline chondrocytes.

The present invention also provides a pharmaceutical composition to be used for arthritis treatment, which includes the chondrocyte pellets prepared by the above-described method, and a method of preventing or treating arthritis.

According to one exemplary embodiment of the present invention, the arthritis is any one or more selected from osteoarthritis, rheumatoid arthritis, psoriatic arthritis, septic arthritis, osteochondritis dissecans, joint and ligament damage and meniscus injury.

According to one exemplary embodiment of the present invention, the pharmaceutical composition may be characterized as being in an injectable form.

According to one exemplary embodiment of the present invention, the pharmaceutical composition may further include hyaluronic acid.

According to one exemplary embodiment of the present invention, the chondrocyte pellets may be administered to a patient using a syringe.

Unless defined otherwise, all technical and scientific terms used herein have the same meanings as usually understood by an expert skilled in the art to which the present invention belongs. Generally, the nomenclature used herein is well known and commonly used in the art.

As a cell therapeutic agent for treating arthritis, to prepare chondrocytes, repeatedly reproducible techniques for forming uniform chondrogenic tissue are needed, and a mass culture system for preparing a considerably large amount of chondrogenic tissue is required to be used for a wide damage site. Therefore, techniques of artificially culturing chondrocytes from stem cells for implantation are being developed.

Stem cells may be roughly divided into embryonic stem cells and adult stem cells according to differentiation ability and the time of generation. Adult stem cells can be obtained from bone marrow, blood, the brain or skin and thus have less ethical problems, but have limited differentiation ability, compared with embryonic stem cells.

Adult stem cells may be divided into multipotent or unipotent stem cells. Representative adult stem cells include mesenchymal stem cells (MSCs) and hematopoietic stem cells. It has been known that MSCs differentiate into chondrocytes, osteoblasts, adipocytes, myocytes, and neurons, and hematopoietic stem cells mainly differentiate into blood cells in the blood, such as red blood cells, white blood cells and platelets.

MSCs refer to stem cells differentiated from the mesoderm resulting from the division of a fertilized egg, and are relatively easily obtained since they are present in cartilage, bone tissue, adipose tissue or bone marrow, and therefore, they are widely used already as a composition for cell therapy for rheumatoid arthritis or osteoarthritis. However, due to a low differentiation rate and an unstable phenotype, MSCs are more likely to undergo unwanted differentiation or transformation during differentiation, and have to be collected in a large amount from a patient. In addition, it has been reported that the mesenchymal stem cells lose their intrinsic characteristics after 3 to 4 days ex vivo, and the production and differentiation abilities of the mesenchymal stem cells differ according to the age of a patient and the status of a disease. Moreover, due to fibrotic cartilage and the expression of hypertrophy-related genes after in vivo implantation, MSCs cause apoptosis and vascular penetration, resulting in calcification of chondrocytes. For this reason, a new cell source for culturing chondrocytes ex vivo is required. Accordingly, in the present invention, human induced pluripotent stem cells (hiPSCs) were selected as a new cell source, and it was confirmed that they have a superior cartilage regeneration effect to MSCs (FIG. 7C).

hiPSCs refer to multifunctional stem cells that can differentiate into all cells or organ tissues of the human body since they differentiate into all three germ layers constituting the living body, and have been prepared to solve many ethical problems of human embryonic stem cells. Since hiPSCs have self-regenerative capacity while maintaining undifferentiation and a normal karyotype, it is determined that they are suitable as a cell source for mass production of a cell therapeutic agent.

Various techniques of preparing chondrocytes from hiPSCs are being developed, and a technique for improving the efficiency of differentiating into chondrocytes by including a process of inducing mesenchymal cells through adherent culture of hiPSCs was developed (Korean Unexamined Patent Application No. 10-2016-0068982). However, a period of adherent and suspension culture performed by treating mesenchymal cells with a chondrogenic factor is at least 39 days, and to obtain fully mature chondrocytes, an additional suspension culture period of 28 days or more is required, and therefore, the preparation of chondrocytes from hiPSCs requires a long period of time. Therefore, the inventors formed an embryoid body (EB) from hiPSCs, induced outgrowth cells (OGs) similar to the mesenchyme from the EB, followed by differentiation into chondrocytes. In the present invention, a period to obtain fully mature chondrocytes by culturing outgrowth cells in a chondrogenic differentiation medium is 30 days, which is much shorter than that of the prior art.

Since culture techniques for maintaining and proliferating undifferentiated hiPSCs are very complicated and take a considerably long time to fully differentiate hiPSCs into specific cells, this has become one of the biggest impediments to the development of related techniques including a differentiation-inducing technique. At the current level, a differentiation-inducing method via manufacture of an embryoid body has been mostly used in a universal differentiation induction technique using hiPSCs. That is, for cell-specific differentiation culture of human induced pluripotent stem cells in vitro, a step of spontaneously aggregating cells into a spherical shape called an embryoid body must be determined in advance, and the embryoid body is used as a common and important medium for induction of lineage-specific differentiation.

Pellet culture is a method of centrifuging a relatively small number of cells to achieve cell aggregation, and artificially forming an ultra-high-density culture system of cells from the initial step of three-dimensional culture. The pellet forming process is simple and easily reproducible, and cells having cartilage-forming ability synthesize and secrete a chondrogenic extracellular matrix under this system, thereby forming chondrogenic tissue.

A technique of forming an embryoid body from hiPSCs and differentiating the EB into chondrocytes was developed, and in this technique, due to unpacking of chondrocyte pellets, an alginate gel was used as a scaffold in a step of culturing pellets and differentiating the pellets into chondrocytes. Therefore, to compare the chondrocyte pellet-forming ability of EB single cells and EB-derived outgrowth cells, the inventors compared the number of chondrocyte pellets formed when an embryoid body is degraded and EB-forming single cells are cultured in a pellet form and when EB-derived outgrowth cells are cultured in a pellet form. As a result, the EB-forming single cells rarely produced chondrocyte pellets, and when the EB-derived outgrowth cells are cultured in a pellet form, a rate of forming chondrocyte pellets was 100% (FIG. 10). From this result, it was confirmed that it is efficient to prepare chondrocyte pellets by inducing outgrowth cells from embryoid bodies.

A technique of confirming a therapeutic effect by injecting chondrocytes differentiated from EB-derived outgrowth cells formed from hiPSCs into an arthritic rat model was developed. In this technique, EB-derived outgrowth cells differentiate into chondrocytes directly without being cultured in a pellet form, and thus the inventors compared chondrocyte differentiation rates when EB-derived outgrowth cells are cultured in a pellet form and then differentiate into chondrocytes and when EB-derived outgrowth cells differentiate into chondrocytes through monolayer culture. As a result, the expression of a gene encoding a main protein constituting the extracellular matrix of cartilage, collagen type II gene (COL2A1), was highly exhibited in chondrocytes undergoing pellet culture, confirming that a rate of differentiation into chondrocytes is higher in the case of pellet culture (FIG. 9).

A technique of forming EB-derived outgrowth cells from hiPSCs and performing monolayer culture and pellet culture to differentiate into a chondrogenic lineage was developed. It has been disclosed that the monolayer culture is an important step for the efficiency of differentiation into chondrocytes, collagen type II was not detected in the chondrocytes obtained by this technique, and since the expression of aggrecan protein was weakly exhibited, chondrocytes which are not fully mature can be obtained. To solve the above-described problems, in the present invention, as a result of pellet culture immediately performed using a chondrogenic differentiation medium containing human bone morphogenetic protein 2 (BMP-2) without a step of monolayer culture of outgrowth cells, it was confirmed that collagen type II and fully mature chondrocytes which show high expression of aggrecan protein can be obtained (FIG. 4).

A technology in which, when EB-derived outgrowth cells are formed from hiPSCs and cultured in a medium containing BMP-2, the efficiency of differentiation into chondrocytes is high was disclosed. However, in the prior art, it was confirmed that EB-derived outgrowth cells differentiate into non-chondrocytes as well as chondrocytes, and there was diversity in the degree of differentiation for each chondrocyte, whereas in the present invention, chondrocyte pellets which have a rate of differentiation into chondrocytes from hiPSCs of 95% or more, have a uniform size, and contain a uniform degree of differentiation were confirmed.

Since the shape and depth of cartilage damage caused by arthritis are not uniform, when artificial cartilage having a three-dimensional structure, prepared in a laboratory, is larger than a damage site, the implant has to be trimmed to the damage shape, and on the other hand, when the cartilage implant is smaller than a damage site, it has to be implanted according to a damaged shape by being pieced together like a mosaic. Although currently developed tissue-engineering cartilage products are implanted by the above-described method, they cannot match the damage thickness, and when an implant is higher or lower than peripheral articular cartilage, due to abnormal weight bearing, additional damage to the implant or normal cartilage around the same is caused. Therefore, when chondrocytes are prepared through pellet culture in an injectable form, they are administered to the damage site in the form of several chondrocyte pellets, and thus can be applied regardless of the shape and thickness of the cartilage damage site. In addition, since chondrocytes are prepared in an injectable form, incision of the cartilage damage site is not required. In this case, since surgery is not required, no recovery period is required, and a simple procedure can not only reduce a patient's pain, but a continuous and effective therapeutic effect can also be exhibited by using a simple procedure. Therefore, the inventors prepared injectable chondrocyte pellets.

To treat arthritis, for application of chondrocytes to a patient by a non-invasive method without an incision at a cartilage damage site, chondrocyte pellets which are smaller than the inner diameter of a clinically available syringe needle and have a uniform size are required.

In the present invention, the size of a syringe needle which can be used in administration of chondrocyte pellets may be 10 to 33 gauge, preferably, 15 to 25 gauge, and most preferably, 17 to 20 gauge. Generally, the size of syringes commonly used for humans in the clinical field are 18-gauge needles with an inner diameter of 573 µm. Accordingly, in order to contain a sufficient amount of chondrocytes which easily pass through the needle, chondrocyte pellets having a size of 500 µm or less are required.

The inventors prepared a chondrocyte pellet consisting of 200 EB-derived outgrowth cells obtained from hiPSCs, which has a diameter of 152 µm, a chondrocyte pellet consisting of 500 EB-derived outgrowth cells obtained from hiPSCs, which has a diameter of 182 µm, a chondrocyte pellet consisting of 1,000 EB-derived outgrowth cells obtained from hiPSCs, which has a diameter of 226 µm, a chondrocyte pellet consisting of 2,000 EB-derived outgrowth cells obtained from hiPSCs, which has a diameter of 278 µm, a chondrocyte pellet consisting of 3,000 EB-derived outgrowth cells obtained from hiPSCs, which has a diameter of 334 µm, and a chondrocyte pellet consisting of 5,000 EB-derived outgrowth cells obtained from hiPSCs, which has a diameter of 462 µm. This means that the chondrocyte pellets of the present invention can be applied in a composition for treating arthritis, which is administered using a syringe.

When outgrowth cells derived from EB obtained from hiPSCs are cultured in a pellet form, in the case of a single cell unit of less than 200 outgrowth cells, it was difficult to culture the cells in a pellet form due to poor cell aggregation. Therefore, the chondrocyte pellets of the present invention may contain 200 to 5,000 outgrowth cells.

The inventors measured a cartilage regeneration effect of pellets containing chondrocytes differentiated from outgrowth cells induced by adherent culture of EB obtained from hiPSCs. In rabbit models with surgery-induced osteoarthritis, it was shown that damaged cartilage is recovered similar to normal tissue by administration of a chondrocyte pellet consisting of 2,000 outgrowth cells. From this result, it was confirmed that the chondrocyte pellet has an excellent cartilage regeneration effect (FIGS. 11 and 12), and thus the present invention was completed.

Therefore, in one aspect, the present invention relates to a method of preparing a chondrocyte pellet, which includes: (a) culturing human induced pluripotent stem cells (hiPSCs) to form and obtain an embryoid body; (b) inducing the embryoid body obtained in Step (a) into outgrowth cells and isolating the same; and (c) culturing the outgrowth cells isolated in Step (b) in a pellet form.

The term "human induced pluripotent stem cell (hiPSC)" used herein refers to a stem cell having a similar level of differentiation ability to an embryonic stem cell, which is made in a method of establishing undifferentiated stem cells having similar differentiation ability to embryonic stem cells using a dedifferentiation technique for human somatic cells. Representative examples of dedifferentiation techniques include fusion with ES cells, somatic cell nuclear transfer and reprogramming by a gene factor.

In the present invention, the term "embryoid body (EB)" refers to a globular stem cell-derived cell mass produced in suspension culture, and due to the ability of potentially differentiating into endoderm, mesoderm and ectoderm, the EB is used as a precursor in most differentiation-inducing processes for ensuring tissue-specific differentiated cells.

The term "outgrowth cell (OG)" refers to a cell extending from an embryoid body when the embryoid body is adherent-cultured in a culture plate coated with an extracellular matrix component to increase cell adhesion.

The term "pellet" refers to an embryoid body-derived outgrowth cell mass formed by three-dimensional culture of a cell aggregate obtained by centrifugation of the cells.

The term "cartilage" includes hyaline cartilage, fibrotic cartilage and elastic cartilage, but the present invention is not limited thereto. The cartilage also includes articular cartilage, ear cartilage, nose cartilage, elbow cartilage, meniscus cartilage, knee cartilage, costal cartilage, ankle cartilage, tracheal cartilage, occipital cartilage and vertebral cartilage, regardless of a cartilage area.

In the present invention, the hiPSCs may be derived from various cells, and preferably, cord blood mononuclear cells (CBMCs).

According to one exemplary embodiment of the present invention, as a result of comparing the expression levels of the aggrecan gene (ACAN) and the collagen type II gene (COL2A1) in a chondrocyte pellet produced from CBMC-derived hiPSCs and a chondrocyte pellet produced from peripheral blood mononuclear cell (PBMC). derived hiPSCs, it was confirmed that the expression level of the chondrocyte pellet produced from CBMC-derived hiPSCs is exceptionally higher. Therefore, it can be seen that a chondrocyte differentiation rate increases when a chondrocyte pellet is prepared from CBMC-hiPSCs (FIGS. 8A-8I).

According to one exemplary embodiment of the present invention, it was confirmed that as the outgrowth cells are cultured in a chondrogenic differentiation medium in the form of a pellet, the expression of COL2A1, ACAN and COMP (cartilage oligomeric matrix protein genes), which are genes encoding main proteins constituting the extracellular matrix (ECM) of cartilage, and SOX9 (sex-determining region Ybox 9 gene), which is a gene encoding a transcription factor regulating their expression, increases (FIG. 4). ACAN is a proteoglycan aggregated in the ECM of cartilage, and induces an interaction with hyaluronan. Collagen type II is a fundamental protein for hyaline cartilage and indicates the characteristics of healthy cartilage.

In addition, according to one exemplary embodiment of the present invention, it was confirmed that the expression levels of the collagen type I gene (COL1A1), which is a representative gene of fibrotic cartilage, and COL10A1, which is a hypertrophic marker, are low in chondrocyte pellets, and the ratio of COL2A1 expression to COL1A1 expression increases (FIGS. 7A-7C). Fibrotic or hypertrophic cartilage is a more mature type which tends to differentiate into bone. This means that the chondrocyte pellets according to the present invention show a higher expression of a gene indicating hyaline cartilage than that of a gene indicating fibrotic cartilage, demonstrating that the chondrocytes according to the present invention have main characteristics of hyaline cartilage.

In the present invention, the culture of Step (a) may be adherent culture. For culture in an ex vivo environment, a surface such as a culture plate coated with the extracellular matrix component for increasing cell adhesion is required.

In the present invention, the induction of Step (b) may be performed on a gelatin-coated plate.

In the present invention, Step (c) may be to centrifuge the isolated outgrowth cells and then culture the cells in a pellet form, and therefore, the cells may be easily cultured in a pellet form by aggregation of the outgrowth cells through centrifugation.

The additional centrifugation may be performed at 1100 to 2500 rpm, preferably 1300 to 2300 rpm, and most preferably 1600 to 2000 rpm.

In the present invention, in Step (c), 95 to 100%, preferably, 96 to 100%, and most preferably 97 to 100% of the isolated cells are formed into a chondrocyte pellet. The sizes of the outgrowth cells contained in a chondrocyte pellet are uniform, and the degrees of differentiation of the outgrowth cells are also uniform.

In the present invention, the formation of EB in Step (a) may be to culture EB in a medium containing fibroblast growth factor 2 (PGF-2).

A fibroblast growth factor is a growth factor inducing potent proliferation ability by stimulating fibroblasts, and there are 23 types of fibroblast growth factors. Among them, FGF-2 is widely distributed in the pituitary gland, brain, kidneys, adrenal gland, placenta, bone matrix, cartilage, endothelial cells and fibroblasts, and has several isotypes. In vertebrates, five isotypes with molecular weights of 18, 22, 225, 24 and 34 kDa are found. Only the 18 kDa type is detected outside cells, but other isotypes are detected inside cells, more specifically, localized in the nucleus. FGF-2 is a peptide playing a very critical role at a physiological level, and involved in development of a fetus, angiogenesis, neuron differentiation and tissue recovery.

In the present invention, the embryoid body of Step (a) may be formed in a medium containing FGF-2 or human transformation growth factor β1 (TGF-β1) at 35 to 39° C. for 4 to 8 days, and preferably, in a medium containing both of the components at 37° C. for 6 days.

According to one exemplary embodiment of the present invention, the medium of Step (a) is prepared by adding glutamine and 4-(2-hydroxyethyl)-1-piperazineethanesulfonic acid (HEPES) to a DMEM/F12 medium containing 543 μl/ml of sodium hydrogen carbonate (NaHCO$_3$), 64 μg/ml of L-ascorbic acid 2-phosphate magnesium, 14 ng/ml of sodium selenite, 107 μg/ml of transferrin, 20 ng/ml of insulin, 100 ng/ml of FGF-2 and 2 ng/ml of TGF-β1.

According to one exemplary embodiment of the present invention, as a result of comparing the pellet-forming ability between EB and EB-derived outgrowth cells, it was confirmed that when EB is degraded into EB single cells to form a pellet, cell aggregation does not occur so that chondrocyte pellets are hardly produced, and when EB-derived outgrowth cells are cultured in a pellet form, a rate of forming chondrocyte pellets is 98% (FIG. 10). Therefore, it can be seen that the culture of EB-derived outgrowth cells in a pellet form is more effective in cell aggregation, compared with the culture of EB in a pellet form.

In the present invention, in Step (b), EB is cultured in a medium containing 20% fetal bovine serum (FBS) or 10% penicillin/streptomycin for 6 to 8 days, and preferably in a medium containing both of the components for 7 days.

In the present invention, the culture in Step (c) is performed in a serum-free medium containing a human bone morphogenetic protein (BMP) and TGF-β.

BMP is a protein factor inducing osteogenesis, and there are 9 types including BMP-1 to 9. Except BMP-1, BMP-2 to 9 belong to the superfamily of TGF-β. The BMP of the present invention may be any one of BMP-1 to 9, and preferably, BMP-2. TGF-β is a growth factor promoting proliferation by transforming normal cells, and plays a regulatory role in cell growth, differentiation and the synthesis of an ECM protein. The TGF-β of the present invention may be any one of TGF-β1 to β3, and preferably TGF-β3.

In the present invention, in Step (c), outgrowth cells are cultured in a chondrocyte differentiation medium containing BMP-2, TGF-β3 or a knockout serum replacement for 25 to 35 days, and preferably, in a medium containing all three components for 30 days.

According to an exemplary embodiment of the present invention, the chondrogenic differentiation medium is prepared by adding 50 ng/ml of BMP-2 and 10 ng/ml of TGF-β3 to a DMEM medium containing a 20% knockout serum replacement, 1× non-essential amino acids, 1 mM L-glutamine, 1% sodium pyruvate, 1% ITS+Premix, 10-7 M dexamethasone, 50 μm ascorbic acid and 40 μg/mL. L-proline, and changed daily for 30 days.

In the present invention, the chondrocyte pellet preferably has a diameter of 100 to 500 μm, more preferably 160 to 400 μm, and most preferably, 200 to 300 μm.

The chondrocyte pellet of the present invention preferably contains 200 to 5,000 outgrowth cells, more preferably, 800 to 3,500 outgrowth cells, and most preferably 1,500 to 2,500 outgrowth cells.

According to one exemplary embodiment of the present invention, as a result of comparing the COL2A1 expression levels in chondrocytes produced by monolayer culture or pellet culture of outgrowth cells derived from EB formed from hiPSCs in a chondrogenic differentiation medium, it was confirmed that COL2A1 was highly expressed in the case of pellet culture (FIG. 9). Therefore, it can be seen that the rate of differentiation into chondrocytes increases when the outgrowth cells are pellet-cultured.

The present invention may provide a pharmaceutical composition for treating arthritis, which includes the chondrocyte pellet prepared by the above-described method.

The term "arthritis" used herein refers to chronic inflammation caused by a defect, damage or loss of cartilage, which means that cartilage, cartilage tissue and/or joint tissue (synovial membrane, articular capsule, subchondral bone, etc.) are injured by mechanical irritation or inflammatory responses. Arthritis includes degenerative joint diseases caused by aging, such as osteoarthritis, autoimmune diseases such as rheumatoid arthritis and psoriatic arthritis, septic arthritis caused by infection, osteochondritis dissecans, joint ligament injury, meniscus injury, but the present invention is not limited thereto.

The term "treatment" used herein refers to (a) inhibition of development of a disorder, disease or symptom; (b) alleviation of a disorder, disease or symptom; or (c) removal of a disorder, disease or symptom.

The pharmaceutical composition of the present invention is a composition which exhibits cartilage regenerative capacity when implanted into a cartilage-defective or injured site to exhibit an improving and therapeutic effect on cartilage damage, and it may be a pharmaceutical composition for treating arthritis alone, or administered with a different pharmacological ingredient to be applied as an adjuvant for treating arthritis.

Therefore, the term "treatment" or "therapeutic agent" used herein means "treatment aid" or "therapeutic supplement."

The pharmaceutical composition for treating arthritis of the present invention includes a pharmaceutically acceptable carrier. The pharmaceutically acceptable carrier included in the pharmaceutical composition of the present invention is conventionally used in formulation, and includes lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, saline, phosphate buffered saline (PBS) or a medium, but the present invention is not limited thereto. In addition to the above components, the pharmaceutically acceptable carrier may further include a lubricant, a wetting agent, a sweetening agent, a flavoring agent, an emulsifier, a suspending agent, and a preservative.

The pharmaceutical composition for treating arthritis of the present invention may be formulated using the pharmaceutically acceptable carrier and/or an excipient in a unit dose type or input in a large capacity container by a method easily executed by those of ordinary skill in the art to which the present invention belongs.

Formulations for parenteral administration include a sterile aqueous solution, a non-aqueous solvent, a suspension, an emulsion, a freeze-dried preparation and a suppository. As a base material for the suppository, Witepsol, Macrogol, Tween 61, cacao butter, laurinum or glycerogelatin may be used.

In the present invention, the pharmaceutical composition may be characterized as being in an injectable form. The injectable form is a form in which a chondrocyte pellet can be administered to a site requiring cartilage regeneration using a syringe without a surgical operation, and more specifically, has a small size enough to pass through an injection needle.

In the present invention, the pharmaceutical composition for treating arthritis may additionally include hyaluronic acid.

According to one exemplary embodiment of the present invention, it was confirmed that, when hyaluronic acid is added to the chondrocyte pellet and then administered to a cartilage damage site, a cartilage regeneration effect is exhibited (FIGS. 12A-12B).

The present invention may also provide a method of preventing or treating arthritis, which includes administering the chondrocyte pellet prepared by the above-described method to an arthritic patient.

The chondrocyte pellet may be administered to a patient at a therapeutically effective amount, the term "therapeutically effective amount" used herein refers to an amount sufficient for treating a disease at a reasonable benefit/risk ratio applicable for medical treatment, and the optimal dosage varies according to factors such as a formulation method, an administration method, a patient's age, body weight, sex, a pathological state, diet, administration time, administration route, excretion rate and response sensitivity, and may be determined by a specialist of ordinary skill in the art considering the above factors. The patient is preferably a mammal including a human, and may also include patient groups which have, have had or are likely to have arthritis without limitation.

The administration is preferably parenteral administration using a syringe, may be administered via a route conventionally used in the medical field, such as intravenous, intraperitoneal, intramuscular, intraarterial, oral, intracardiac, intramedullary, intrathecal, transdermal, intestinal, subcutaneous, sublingual or local administration, and most preferably, intra-articular administration.

Advantageous Effects

A chondrocyte pellet derived from human induced pluripotent stem cells (hiPSCs) of the present invention has a considerably high rate of differentiation into chondrocytes, a uniform size and a uniform degree of differentiation, a pharmaceutical composition for treating arthritis, which includes the same, has an excellent cartilage regeneration effect when administered to a cartilage damage site, and has an injectable form that does not require surgery. Therefore, by using the pharmaceutical composition, the patient's pain cannot only be alleviated with a simple procedure, but also a continuous effect of treating arthritis after the procedure is provided.

BRIEF DESCRIPTION OF DRAWINGS

FIGS. 12A-12B show the result (destruction score) of evaluating cartilage states 4 weeks after injection of a minimal injectable unit (MIU), which is a chondrocyte pellet containing 2,000 outgrowth cells, and/or hyaluronic acid (HA) into a cartilage damage model using an ICRS score method, and an evaluation process thereof, indicating the cartilage regeneration effect of chondrocyte pellets produced from CBMC-hiPSCs according to the present invention.

DETAILED DESCRIPTION

Example 1

Figure 1:
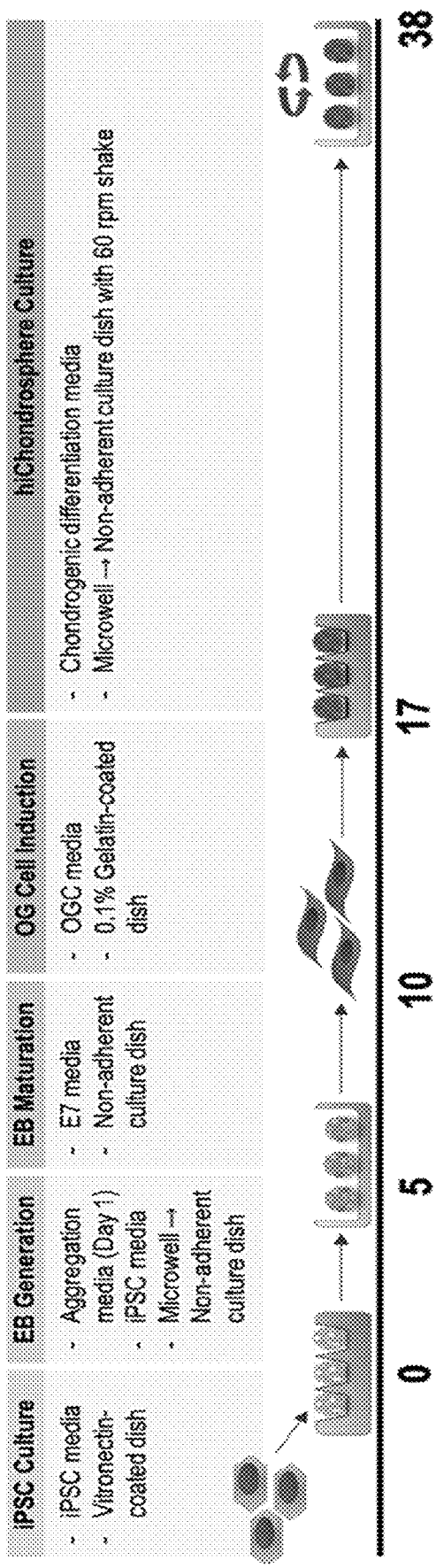
FIG. 1 is a schematic diagram illustrating a process of preparing a 3D chondrocyte cluster having a size that can pass through a syringe using induced pluripotent stem cells of the present invention.
Figure 2:
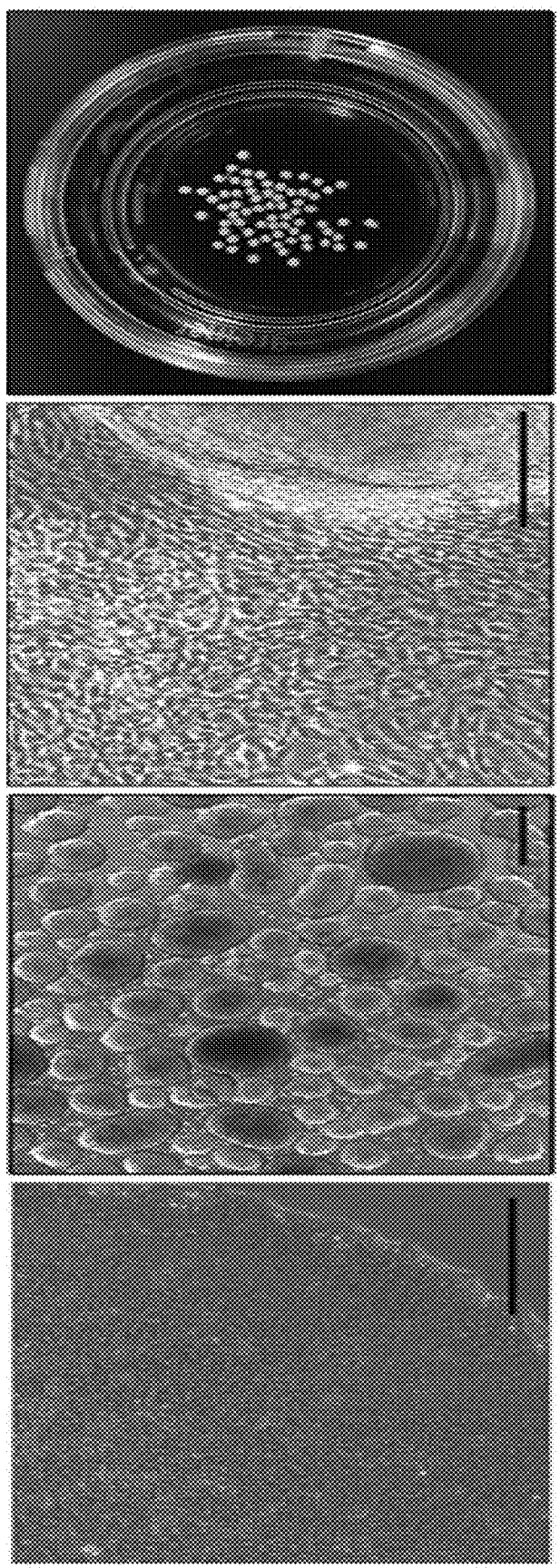
FIG. 2 shows an image of CBMC-derived human induced pluripotent stem cells (hiPSCs), an image of a formed embryoid body, an image of outgrowth cells derived from an embryoid body adhered to a gelatin-coated culture plate, and an image of prepared chondrocyte pellets in order from left to right.
Figure 3:
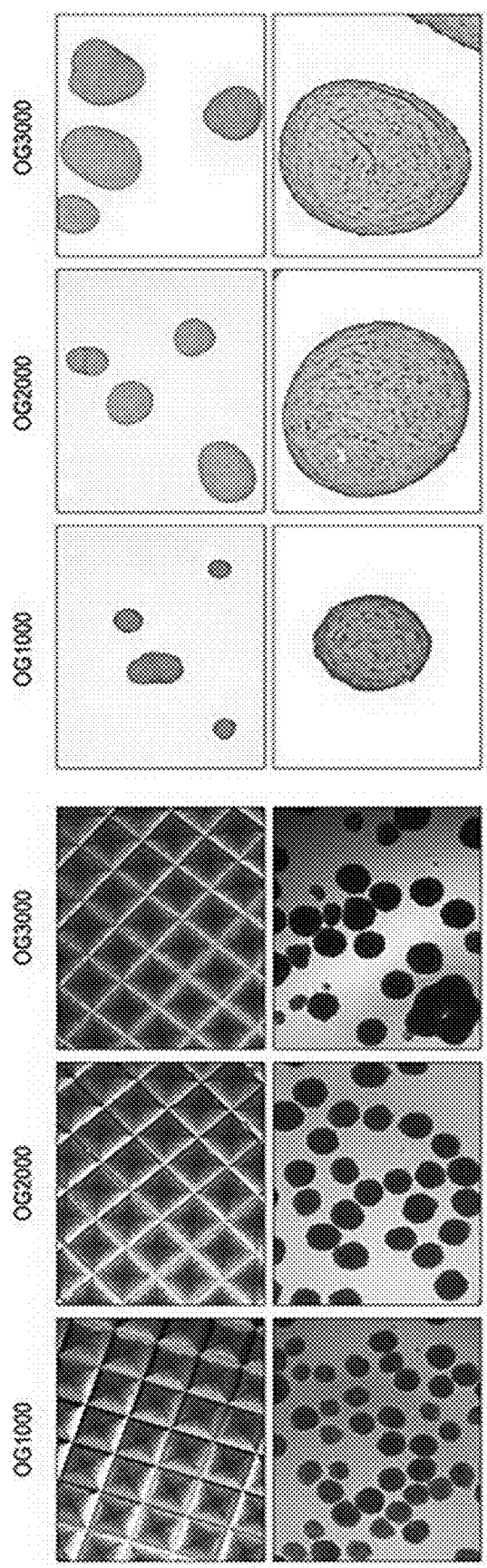
FIG. 3 shows images of pellets made of 1,000, 2,000 and 3,000 outgrowth cells produced in microwells and chondrocyte pellets cultured in a chondrogenic differentiation medium, stained with toluidine blue.

Preparation of Human Induced Pluripotent Stem Cells

Human induced pluripotent stem cells (hiPSCs) were prepared from cord blood mononuclear cells (CBMCs). CBMCs used herein were obtained from the Cord Blood Bank of St. Mary's Hospital in Seoul, Korea. Cord blood was diluted with phosphate buffered saline (PBS), centrifuged at 850×g for 30 minutes through a Ficoll gradient to collect CBMCs, and then the obtained CBMCs were stored until use after washing and freezing. CBMCs were thawed immediately before use, and resuspended in a CC110 cytokine cocktail (STEMCELL)-added StemSpan medium (STEMCELL Technological, Vancouver, British Columbia, Canada), and then cultured at 37° C. in a 5% $CO_2$ incubator for 5 days.

The cultured CBMCs were seeded in a 24-well plate at a concentration of $3\times10^5$ cells/well, and then reprogramming was induced according to a protocol provided by the manufacturer using a CytoTune™-iPS 20 Sendai Reprogram Kit (A16518, Life Technologies), thereby obtaining CBMC-derived hiPSCs.

The obtained hiPSCs were cultured in a vitronectin-coated container (Thermo Fisher Scientific, Waltham, MA, USA), and a culture medium was cultured while the culture medium was replaced with a TeSR-E8 medium (STEMCELL Technologies) once a day.

Example 2

Formation of Embryoid Body from hiPSCs

The CBMC-derived hiPSCs prepared in Example 1 were resuspended in an Aggrewell medium (STEMCELL), and seeded in a 100-mm culture plate at a concentration of $2\times10^6$ cells/well. The seeded hiPSCs were incubated in a 37° C. incubator for 24 hours, and the following day, the culture medium was replaced with a TeSR-E8 medium (glutamine and 4-(2-hydroxyethyl)-1-piperazineethanesulfonic acid (HEPES) were added to a DMEM/F12 medium containing 543 µl/ml of sodium hydrogen carbonate ($NaHCO_3$), 64 µg/ml of L-ascorbic acid 2-phosphate magnesium, 14 ng/ml of sodium selenite, 107 µg/ml of transferrin, 20 ng/ml of insulin, 100 ng/ml of fibroblast growth factor-2 (FGF-2) and 2 ng/ml of transforming growth factor beta 1 (TGF-β1)), followed by forming and obtaining an embryoid body (EB) by further adherent culture for 6 days.

Example 3

Formation and Isolation of Outgrowth Cells from EB

The EB formed and obtained in Example 2 was suspended in a DMEM medium (Thermo Fisher Scientific) containing 20% fetal bovine serum and 10% penicillin/streptomycin, and cultured on a gelatin-coated plate in 5% $CO_2$ at 37° C. for 7 days to induce the formation of outgrowth cells (OGs). To this end, the bottom surface of a culture plate was coated with 0.1% gelatin for 30 minutes, and completely dried before use.

The formed OGs were separated from the gelatin-coated plate, passed through a 40-µm cell strainer (Thermo Fisher Scientific) to remove an EB clump, thereby isolating and obtaining a single cell unit of OGs.

Example 4

Preparation of Chondrocyte Pellets from OGs and Differentiation into Chondrocytes The single cell units of OGs isolated and obtained in Example 3 were counted and plated in a microwell to reach $1\times10^3$, $2\times10^3$ or $3\times10^3$ cells/well per pellet, and then centrifuged at 1800 rpm for 5 minutes to facilitate the aggregation of cells in a pellet form, thereby preparing chondrocyte pellets. As a result of measuring diameters of the prepared pellets, it was confirmed that the diameter of the pellet consisting of 200 OGs is 152 µm, the diameter of the pellet consisting of 500 OGs is 182 µm, the diameter of the pellet consisting of 1,000 OGs is 226 µm, the diameter of the pellet consisting of 2,000 OGs is 278 µm, the diameter of the pellet consisting of 3,000 OGs is 334 µm, and the diameter of the pellet consisting of 5,000 OGs is 462 µm.

Afterward, the prepared chondrocyte pellets were inoculated in a chondrogenic differentiation medium, replaced with a fresh medium once a day, and incubated at 37° C. for a total of 30 days, thereby finally obtaining differentiated chondrocytes. As the chondrogenic differentiation medium, a DMEM medium (20% knockout serum replacement, 1× non-essential amino acids, 1 mM L-glutamine, 1% sodium pyruvate, 1% ITS+Premix, $10^{-7}$M dexamethasone and 50 µm ascorbic acid, 40 µg/ml L-proline) to which 50 ng/ml human bone morphogenetic protein 2 (BMP2) and 10 ng/ml human transforming growth factor beta 3 (TGF-β3) were added was used.

Example 5

Analysis of Genetic Characteristics of Chondrocyte Pellets

To analyze the genetic characteristics of the chondrocyte pellets obtained in Example 4, the expression levels of genes encoding main proteins constituting the extracellular matrix of cartilage, such as the collagen type II gene (COL2A1), the aggrecan gene (ACAN), the cartilage oligomeric matrix protein gene (COMP) and the sex-determining region Y-box 9 gene (SOX9) in chondrocyte pellets on day 10, 20 and 30 were analyzed.

Figure 4:
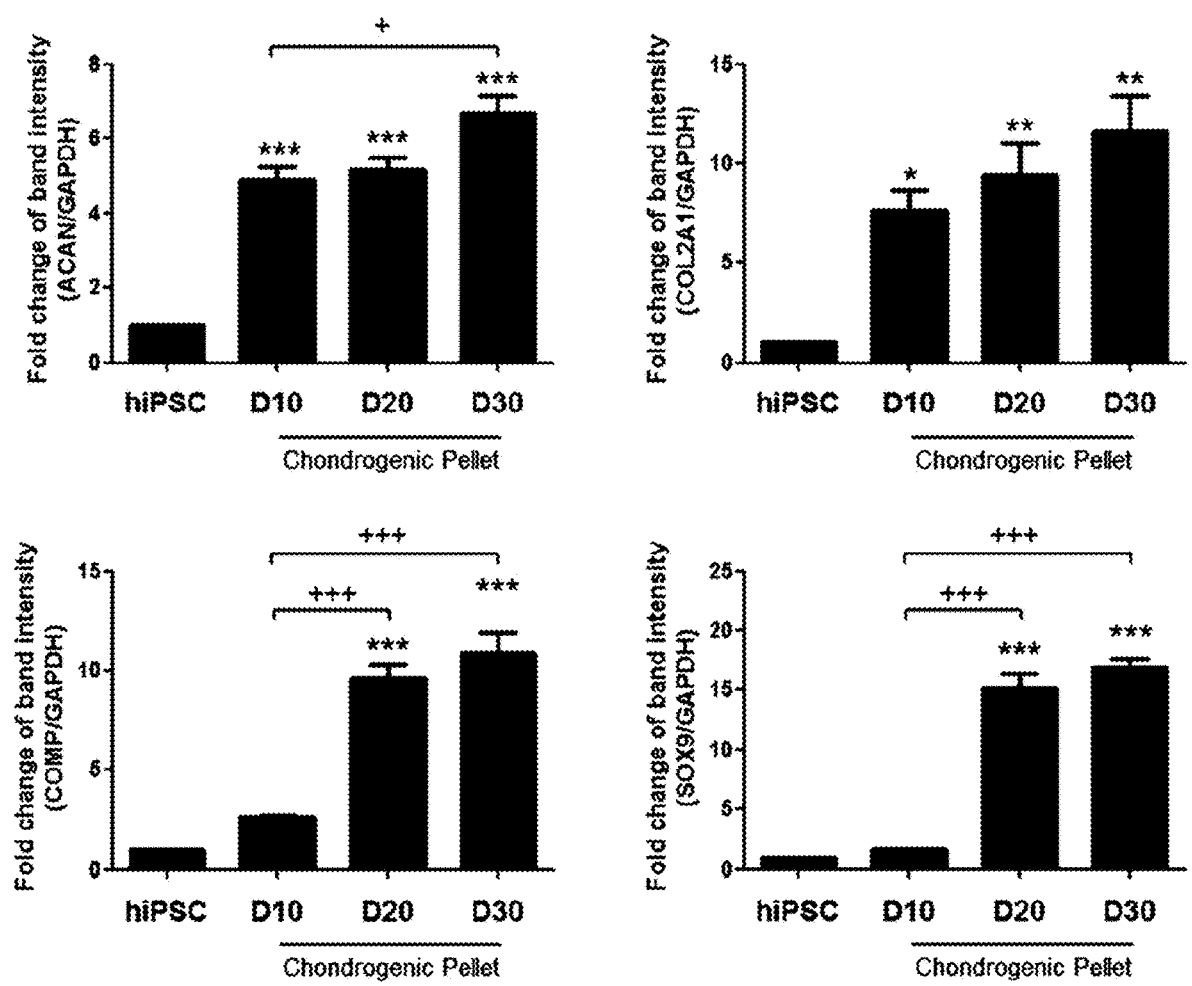
FIG. 4 shows genetical characteristics of chondrocyte pellets produced from CBMC-hiPSCs according to the present invention, and shows the results of measuring the expression levels of the collagen type II gene (COL2A1), the aggrecan gene (ACAN), the cartilage oligomeric matrix protein gene (COMP) and the sex-determining region Y-box 9 gene (SOX9) in chondrocyte pellets on day 10, 20 and 30 of culture in a chondrogenic differentiation medium (*, +p<005, , ++p<001, *, +++ p<0001).

As a result, as shown in FIG. 4, it was confirmed that the expression of ACAN, COL2A1 and COMP significantly increase in the chondrocyte pellets of the present invention, compared with hiPSCs. Accordingly, it was confirmed that the chondrocyte pellets prepared according to the present invention synthesize an ECM component of cartilage, and cartilage-like characteristics are exhibited.

Example 6

Histological Analysis of Chondrocyte Pellets

For histological analysis of the chondrocyte pellets obtained in Example 4, the pellets were fixed using 4% paraformaldehyde at room temperature for 2 hours. One layer of gauze was placed on a cassette, and then the chondrocyte pellets were transferred to the gauze. Subsequently, dehydration was performed using an ethanol solution. The dehydration solution was removed with graded ethanol solutions and a xylene mixture (Duksan Pure Chemicals, Ansan, Korea), and paraffin was solidified overnight. The following day, the chondrocyte pellets were embedded in a paraffin block, and a 7-µm section was obtained using a microtome. A slide was dried at 60° C. for 10 minutes. The section was deparaffinated in two cycles with xylene. The section was rehydrated with a gradually-decreasing ethanol series, and rinsed under running tap water for 5 minutes.

To detect the ECM in cartilage, for Alcian blue staining, a section was incubated in a 1% Alcian blue solution for 30 minutes. Afterward, the slide was washed, and then counter-stained with nuclear fast red for 1 minute. For Safranin O staining, a section was incubated on a slide in Weigert's iron hematoxylin for 10 minutes. The slide was washed, and then incubated in a 0.1% safranin solution for 5 minutes. For toluidine staining, a section was incubated in a toluidine blue solution for 4 minutes.

After the staining process, the section was washed and passed through a gradually-increasing ethanol series. The ethanol was removed with xylene in two cycles, and the slide was fixed using a VectaMount™ permanent mounting medium (Vector Laboratories, Burlingame, CA, USA). Stained states of the chondrocyte pellets were confirmed with a bright field microscope.

As a positive control, the chondrocyte pellets prepared from bone marrow-derived mesenchymal stem cells (BMSCs) by the same methods as described in Examples 2 to 4 were used.

Figure 5:
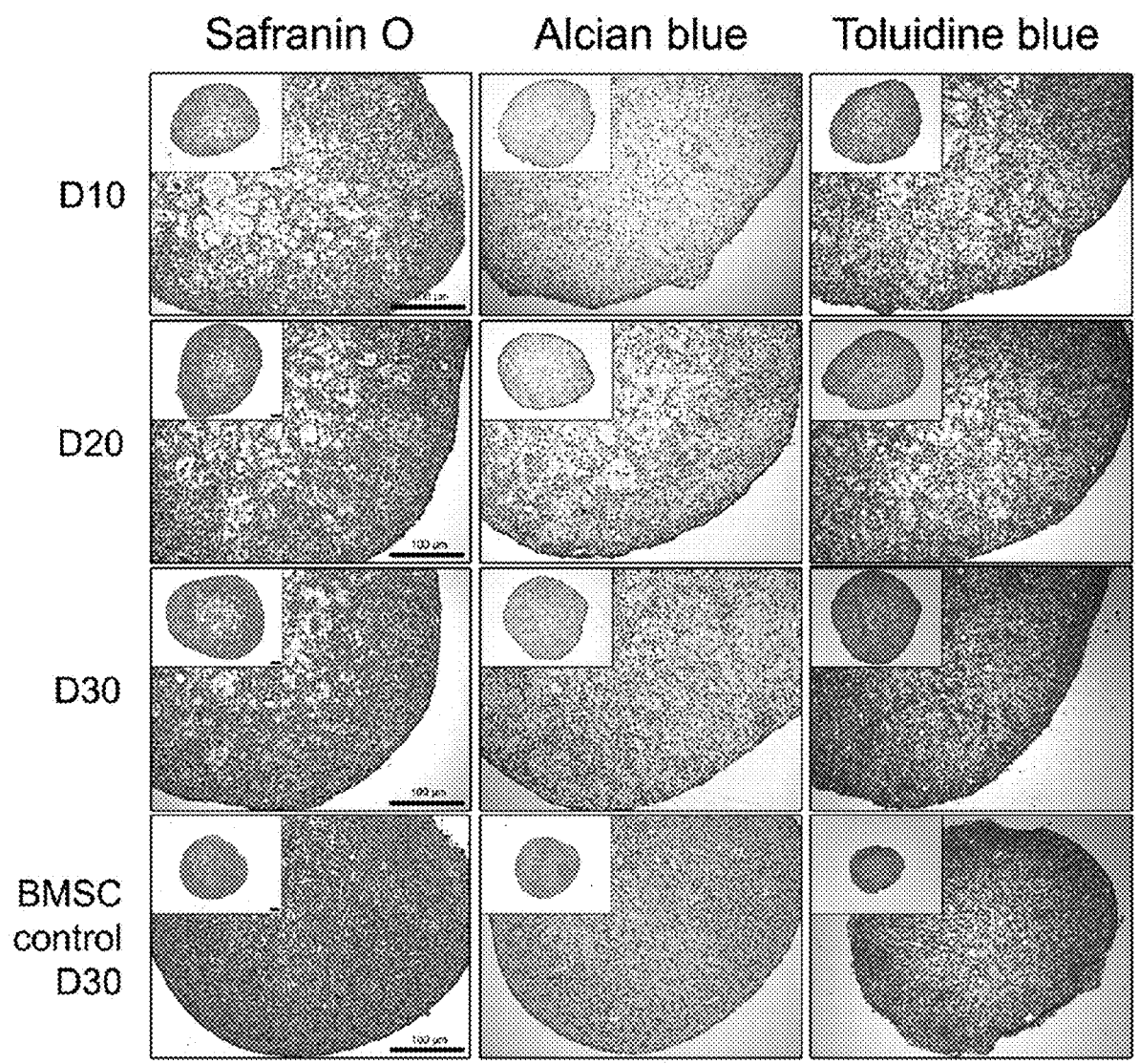
FIG. 5 shows the result of histological analysis for chondrocyte pellets produced from CBMC-hiPSCs according to the present invention, and are images of pellets stained with Safranin O, Alcian blue and Toluidine blue on day 10, 20 and 30 of culture in a chondrogenic differentiation medium.

As a result, as shown in FIG. 5, even at the early stage of differentiation (on day 10), ECM accumulation was confirmed in the inner part of the chondrocyte pellets. Lacunae is one of the major characteristics exhibited in articular cartilage. Cavities such as empty lacunae were generated after day 10. However, the size decreased as differentiation into chondrocytes progressed. On day 30 of differentiation, as ECM was accumulated in an empty cavity, it appears similar to the lacunae in the articular cartilage.

Example 7

Immunohistochemical Analysis of Chondrocyte Pellets

For immunohistochemical analysis for the chondrocyte pellets obtained in Example 4, a section obtained by the same method as described in Example 6 was dried at 60° C. for 2 hours, and deparaffinated with xylene in two cycles. The section was rehydrated with a gradually-decreasing ethanol series, and then rinsed under running tap water for 5 minutes.

Antigen unmasking was induced by incubation in boiled citrate buffer (Sigma-Aldrich) for 15 minutes, and cooling for 20 minutes. Subsequently, the cooled section was washed twice with deionized water (DW). The activity of endogenous peroxidase was blocked by incubating the section in 3% hydrogen peroxide (Sigma-Aldrich) diluted with DW for 10 minutes. The section was washed twice with DW, and then additionally washed with 0.1% Tween 20-containing tris-buffered saline (TBS; TBST). The section was blocked with TBS containing 1% bovine serum albumin (Sigma-Aldrich, St Louis, MO, USA) at room temperature for 20 minutes.

The primary antibody diluted with a blocking solution was added to the section and then incubated overnight at 4° C. The primary antibody was diluted in the following ratios; Collagen type I (1/100; Abcam), Collagen type II (collagen type II, 1/100; Abcam) and Aggrecan (1/100; GeneTex, Irvine, CA, USA). A negative control slide was treated with the same amount of antibody-free blocking solution. The following day, the section was washed with TBST three times for 3 minutes, and a secondary antibody (1/200; Vector Laboratories) was applied at room temperature for 40 minutes. The section was washed with TBST, and incubated in an ABC reagent (Vector Laboratories) for 30 minutes. A slide was washed three times with TBST, and a DAB solution (Vector Laboratories) was applied for 1 minute. The section was washed with DW until the color washed out. For counter staining, Mayer's hematoxylin was applied to the section for 1 minute. The section was washed, and then passed through a gradually-increasing ethanol series. The ethanol was removed with xylene in two cycles, and the slide was fixed using a VectaMount™ permanent mounting medium (Vector Laboratories, Burlingame, CA, USA). Stained states of the chondrocyte pellets were confirmed with a bright field microscope.

The quality of cartilage is determined by the main type of ECM protein. Accordingly, it is important to confirm a specific protein. Aggrecan and collagen type II proteins are known as main components constituting ECM. The collagen type II is the major collagen type indicating hyaline cartilage.

Figures 6A, 6B:
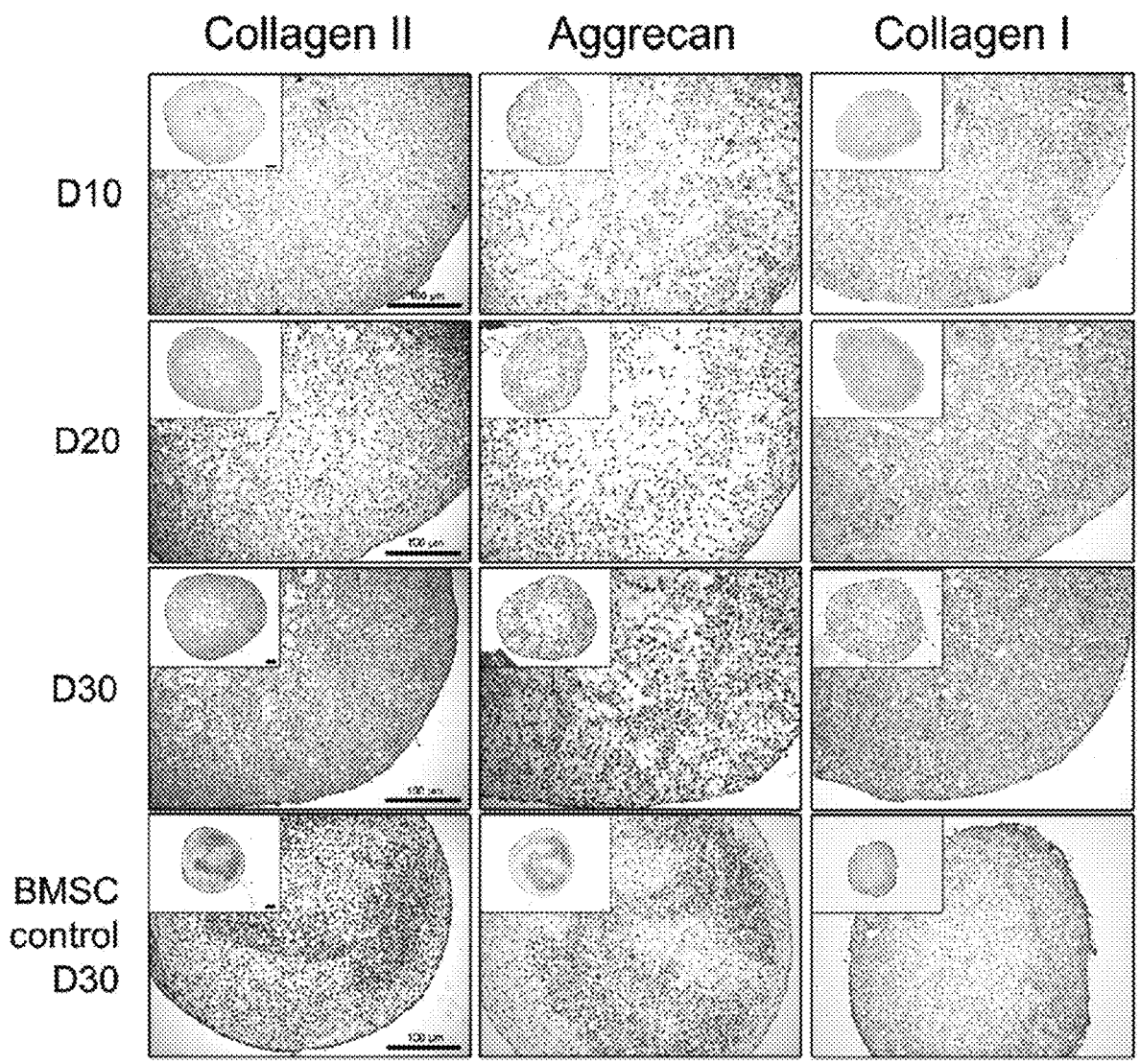
FIGS. 6A-6B show the result of immunohistochemical analysis for chondrocyte pellets produced from CBMC-hiPSCs according to the present invention: a shows images of chondrocyte pellets stained with antibodies against collagen type II and Aggrecan on day 10, 20 and 30 of culture in a chondrogenic differentiation medium; and b shows images of chondrocyte pellets stained with antibodies against collagen type I.
Figures 7A, 7B, 7C:
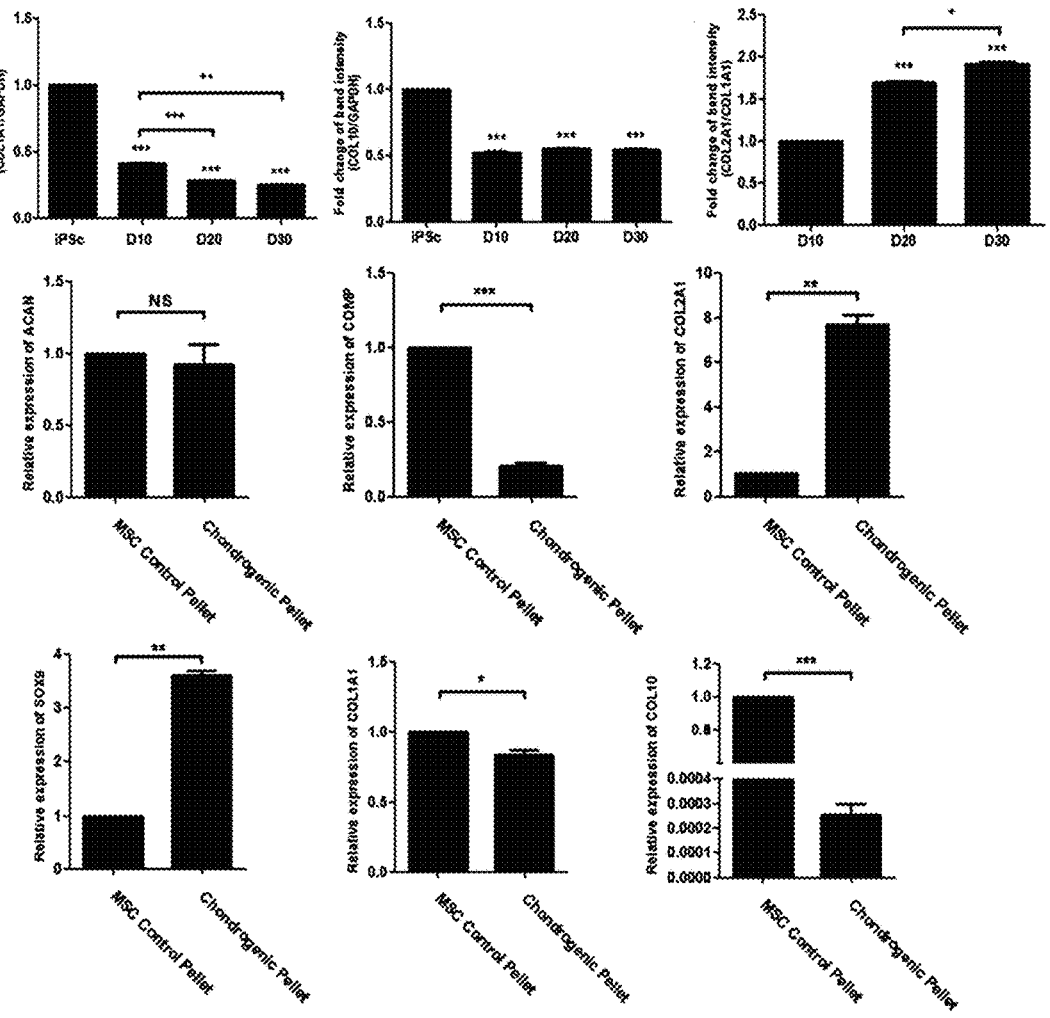
FIGS. 7A-7C show the result of additional analysis for genetic markers of chondrocyte pellets produced from CBMC-hiPSCs or mesenchymal stem cells (MSCs) according to the present invention: a shows the results of measuring the expression levels of the collagen type I gene (COL1A1), which is a representative gene of fibrotic cartilage, and COL10A1, which is a hypertrophic marker, in hiPSCs and chondrocyte pellets on day 10, 20 and 30 of culture in a chondrogenic differentiation medium, b shows the expression levels of COL2A1 and COL1A1 in chondrocyte pellets on day 10, 20 and 30 of culture in a chondrogenic differentiation medium; and c shows the results of measuring the relative expression levels of ACAN, COMP, COL2A1, SOX9, COL1A1 and COL10A1 in chondrocyte pellets produced from MSC or CBMC-derived hiPSCs on day 30 of culture in a chondrogenic differentiation medium (*, +p<005, , ++p<001, *, +++p<0001).
Figures 8A, 8B, 8C, 8D, 8E, 8F, 8G, 8H, 8I:
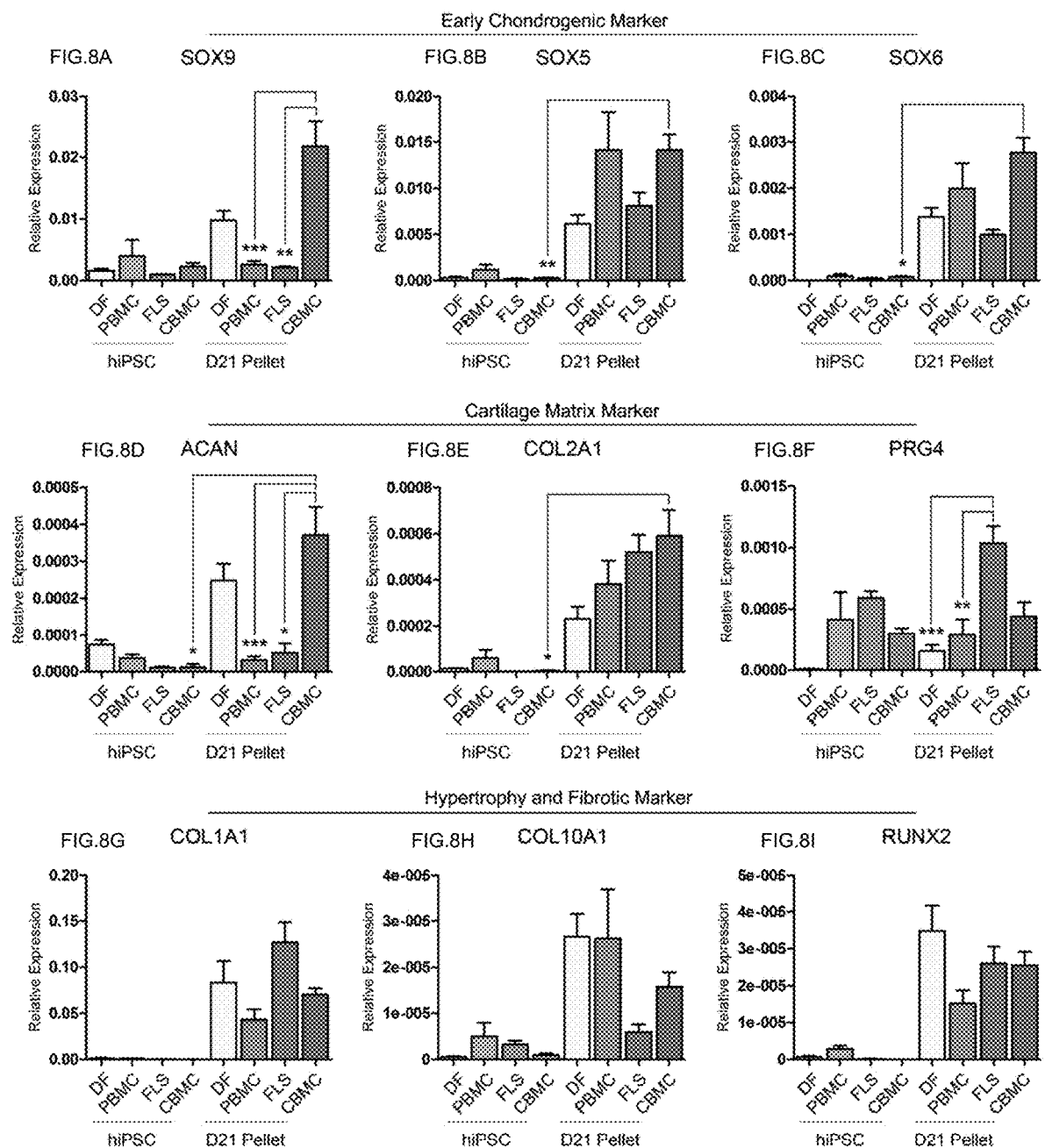
FIGS. 8A-8I show the results of confirming the expression of an early chondrogenic marker, a cartilage matrix marker and a hypertrophy and fibrotic marker in cartilage pellets prepared from hiPSCs derived from various cell lines (DF is derived from skin fibroblasts, PBMC is derived from peripheral blood monocytes, FLS is derived from osteoarthritis fibroblast-like cells, and CBMC is derived from cord blood monocytes). SOX9, SOX5 and SOX6 are identified as early chondrogenic markers, ACAN, COL2A1 and PRG4 are identified as cartilage matrix markers, and COL1A1, COL10A1 and RUNX2 are identified as fibrotic cartilage markers.

As a result, as shown in FIG. 6, it was confirmed that the staining intensity of the collagen type II was much higher in CBMC-hiPSC-derived chondrocyte pellets, compared with a BMSC control. Corresponding to the staining result, aggrecan and collagen type II were mostly detected inside the chondrocyte pellets on day 30. The main characteristic of fibrotic cartilage is high expression of collagen type I. Accordingly, it was confirmed that the chondrocyte pellets obtained in Example 4 do not have the main characteristic of the fibrotic cartilage (FIG. 7B). The expression of the collagen type I was relatively higher than the BMSC control pellets, but maintained at a constant level and did not greatly increase during differentiation into chondrocytes.

The chondrocytes differentiated from CBMC-hiPSCs were able to produce an ECM component protein, and the expression of collagen type II was higher than that of collagen type I. As a result, it was confirmed that CBMC-hiPSCs can produce chondrocytes having similar characteristics of hyaline cartilage.

Example 8

Comparison of Gene Expression of Chondrocyte Pellets Produced from CBMC-hiPSCs and MSCs Collagen is the most abundant protein constituting the ECM. There are various types of collagens, but collagen type I, II and X are usually related to cartilage. In Example 7, the expression of collagen type I and collagen type II was confirmed by immunohistochemical analysis (FIGS. 6A and 6B). Based on this, the expression of COL1A1 and a protein known as a dominant type expressed in hypertrophic cartilage, that is, COL10A1, was analyzed. The COL1A1 expression was reduced every observation time point, and the COL10A1 expression was not changed during differentiation into chondrocytes (FIG. 7A).

An expression ratio of COL2A1 to COL1A1 was measured, and it could be confirmed that the expression ratio of COL2A1 to COL1A1 increases (FIG. 7B), indicating that the expression of a hyaline cartilage gene is higher than that of a fibrotic cartilage gene. The chondrocyte pellets produced from CBMC-hiPSCs were compared with chondrocyte pellets produced from MSCs (MSC control pellets) using real-time PCR (FIG. 7C). The expression of COL2A1 and SOX9 was significantly higher in the chondrogenic pellets, compared with the MSC control pellets. On the other hand, the expression of the fibrotic marker COL1A1 and the hypertrophic marker COL10A1 was remarkably higher in the MSC control pellets. Therefore, it was confirmed that CBMC-hiPSCs are more suitable for production of chondrocytes for hyaline cartilage regeneration, compared with MSCs.

Example 9

Comparison of Chondrocyte Differentiation Ability of Various hiPSCs

To compare chondrocyte differentiation ability of hiPSCs derived from various cells, chondrocyte pellets were prepared from dermal fibroblast (DF)-derived, peripheral blood monocyte (PBMC)-derived, osteoarthritis fibroblast-like cell (FLS)-derived or cord blood monocyte (CBMC)-derived hiPSCs in a chondrogenic differentiation medium (Example 4) for 21 days according to the same methods as described in Examples 1 to 4. In each chondrocyte pellet (D21 pellet), the expression levels of an early chondrogenic marker, a cartilage matrix marker and a hypertrophic or fibrotic cartilage marker, which are associated with cartilage formation, were compared, and specifically, SOX9, SOX5 and SOX6 as early chondrogenic markers, ACAN, COL2A1 and PRG4 as cartilage matrix markers, and COL1A1, COL10A1 and RUNX2 as hypertrophic or fibrotic cartilage markers were confirmed.

As a result, as shown in FIGS. 8A-8I, in CBMC-hiPSCs, the expression levels of the early chondrogenic markers and the cartilage matrix markers, such as SOX9, SOX5, SOX6, ACAN and COL2A1 were highest, and the expression levels of the hypertrophic or fibrotic cartilage markers, such as COL1A1, COL10A1 and RUNX2, were relatively lower, compared with the three other types of hiPSC-derived chondrocyte pellets.

Example 10

Comparison of Chondrocyte Differentiation Ability Between EB-Derived OG Pellet and EB-Derived OGs To compare the chondrocyte differentiation ability in the case of the monolayer culture of EB-derived OGs and the case of pellet culture, $1 \times 10^5$, $3 \times 10^5$ or $5 \times 10^5$ of the single cell unit of OGs obtained in Example 3 were cultured by monolayer culture of in a pellet form in the chondrogenic differentiation medium of Example 4 for 21 days. The expression levels of SOX9, ACAN, COL2A1, COL1A1 and COL10A1 were compared in the chondrocytes obtained by monolayer culture or pellet culture.

Figure 9:
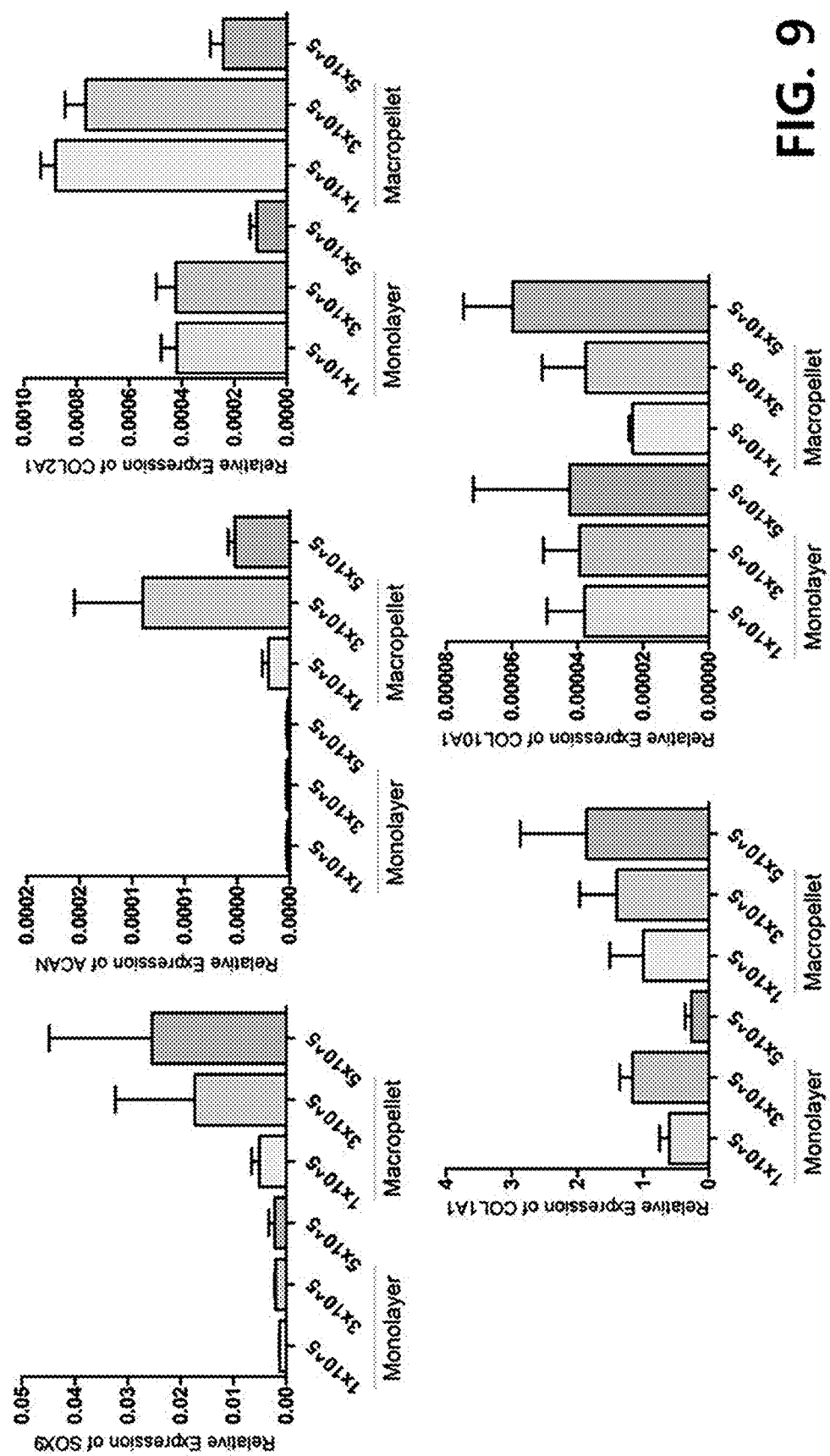
FIG. 9 shows the result of comparing the expression levels of SOX9, ACAN, COL2A1, COL1A1 and COL10A1 by measuring the numbers ($1 \times 10^5$, $3 \times 10^5$ and $5 \times 10^5$) of chondrocytes produced by monolayer culture of embryoid body (EB)-derived outgrowth cells in a chondrogenic differentiation medium according to the present invention and chondrocytes produced by culturing EB-derived outgrowth cells in a pellet form (Macropellet).

As a result, as shown in FIG. 9, when all of $1 \times 10^5$, $3 \times 10^5$ and $5 \times 10^5$ of the OGs were cultured in a pellet form, the expression levels of SOX9, ACAN and COL2A1 were high. Accordingly, when the EB-derived OGs were cultured in a pellet form, high chondrocyte differentiation ability was confirmed.

Example 11

Comparison of Chondrocyte Pellet-Forming Ability of EB Single Cells and EB-Derived OGs To compare the chondrocyte pellet-forming ability between EB single cells and EB-derived OGs, the numbers of chondrocyte pellets obtained when single cells constituting EB, obtained by degrading EB, were cultured in a pellet form in a chondrogenic differentiation medium and when EB-derived OGs are cultured in a pellet form were compared.

Figure 10:
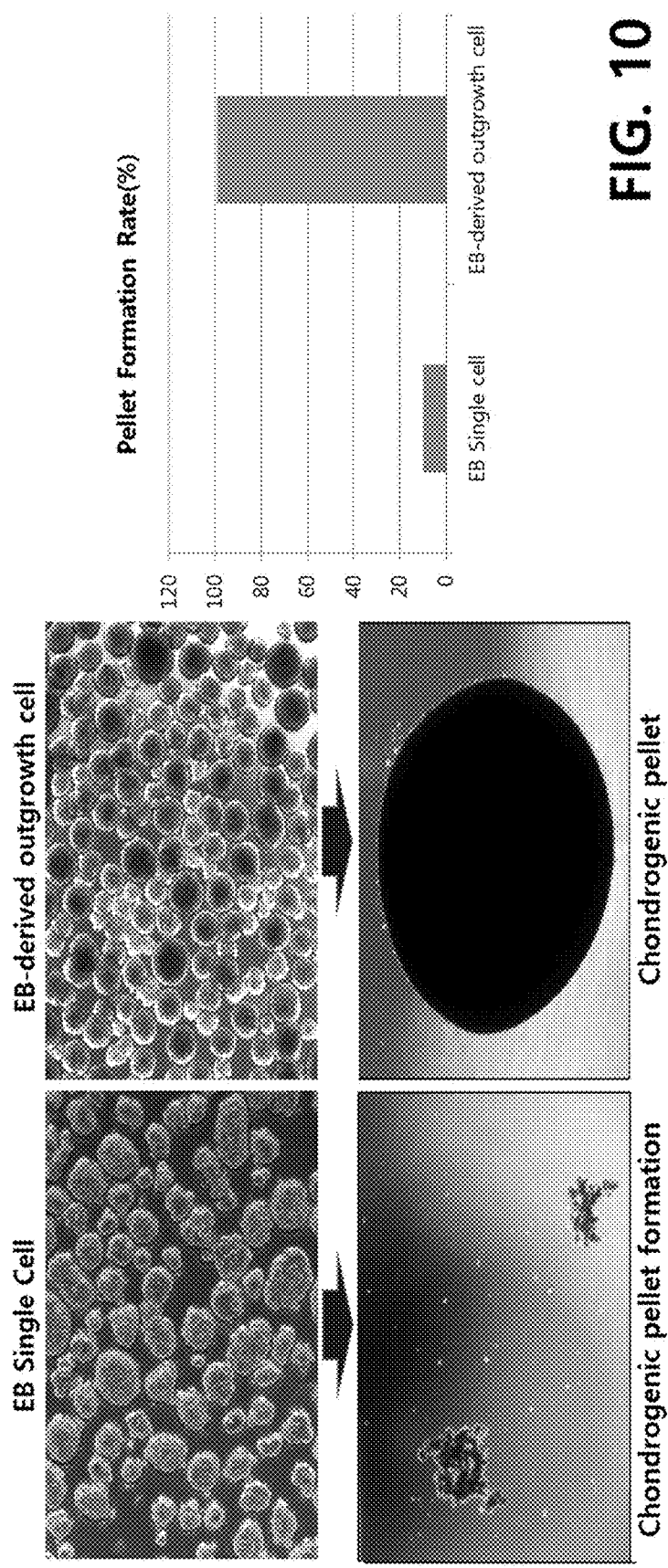
FIG. 10 shows the result of comparing the chondrocyte pellet-forming ability of EB single cells and EB-derived outgrowth cells according to the present invention. This shows images of chondrocyte pellets formed when single cells constituting EB are cultured in a pellet form in a chondrogenic differentiation medium by degrading the EB and when EB-derived outgrowth cells are cultured in a pellet form and pellet formation rates of the formed chondrocytes.

As a result, as shown in FIG. 10, when the single cells constituting EB were cultured in a pellet form, a chondrocyte pellet formation rate was approximately 11%, and when the EB-derived OGs were cultured in a pellet form, a chondrocyte pellet-forming rate was approximately 98%. Accordingly, it could be confirmed that chondrocyte pellets were efficiently prepared by inducing OGs from EB.

Example 12

Analysis of Cartilage Regeneration Effect in Osteoarthritis Models

It was intended to evaluate the cartilage regeneration effect of the chondrocyte pellets prepared in Example 4 in osteoarthritis animal models.

Specifically, a surgically-induced model was established by a method of developing osteoarthritis by inducing joint injury through a surgical procedure for the collateral or cruciate ligament. Meniscectomy and anterior cruciate ligament transection (ACLT) are generally used. The inventors induced the injury of the cartilage region similar to osteoarthritis naturally occurring in a rabbit through ACLT. Three days after ACLT, a minimal injectable unit (MIU), which is a chondrocyte pellet containing 2,000 OGs, hyaluronic acid (HA), or both of MIU and HA (HA+MIU) was administered by intra-articular injection. Sham control is a rabbit which is re-sutured without damage to the cartilage region after laparotomy. 30 days after administration of MIU and/or HA, the cartilage region was stained with safranin O and toluidine blue to confirm a cartilage regeneration effect.

Figure 11:
FIG. 11 shows a result of preparing a rabbit model as an osteoarthritis model by anterior cruciate ligament transection (ACLT), and administering chondrocyte pellets (MIU) and/or hyaluronic acid (HA) into the rabbit by intra-articular injection.
Figure 11:
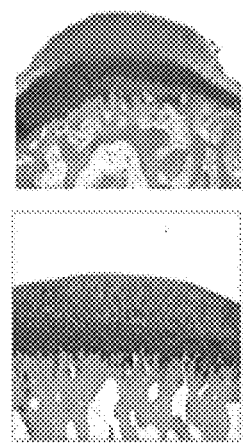

As a result, as shown in FIG. 11, when MIU only or both of MIU and HA was administered with a syringe, it was confirmed that a lot of cartilage-specific matrix was synthesized in a cartilage damage site, thereby regenerating cartilage tissue similar to normal tissue. The regenerated cartilage was stained red or blue. Accordingly, the chondrocyte pellets of the present invention exhibit an excellent cartilage regeneration effect, and particularly, it could be confirmed that MIU only or both of MIU and HA results in an excellent cartilage regeneration effect, compared with an HA-only administered group.

Example 13

Analysis of Cartilage Regeneration Effect in Osteoarthritis Models

An osteoarthritis rabbit model was established by the same method as described in Example 12. Four weeks after injection of MIU and/or HA, cartilage of the rabbit was stained with Evans blue, and the scores evaluated by three people by a blind test were summed and then averaged by ICRS scoring, which is a method generally used for measurement of a cartilage state. ICRS scores are shown in Table 1 below, and a higher score indicates a higher degree of causing osteoarthritis, that is, degree of cartilage damage (0=normal; 1=superficial fissures and cracks; 2=lesions extending down to <50% of cartilage depth; 3=cartilage defects extending down>50% of cartilage depth; 4=severely abnormal).

As a result, as shown in Table 1 and FIGS. 12A-12B, it could be confirmed that when MIU only was administered, the degree of cartilage damage was significantly low on average, compared with a HA-only administered group or MIU and HA-co-administered group.

TABLE 1

| Animal No. | Control (Sham) | Osteoarthritis model (VC) | HA | MIU | MIU + HA |
|---|---|---|---|---|---|
| 1 | 1 | 15 | 21 | 0 | 9 |
| 2 | 0 | 59 | 23 | 16 | 35 |
| 3 | 0 | 18 | 21 | 10 | 7 |
| 4 | 0 | 16 | 13 | 10 | 8 |
| 5 | 0 | 26 | 22 | 12 | 27 |
| Average | 0.2 | 26.8 | 20 | 8.8 | 17.2 |

In the above, specific parts of the specification have been described in detail, although it is clear to those skilled in the art that this specific technique is merely a preferred embodiment and the scope of the specification is not limited thereto. Thus, the substantial scope of the specification will be defined by the accompanying claims and their equivalents.

Since chondrocyte pellets provided in the present invention have a uniform and small size, they may be administered to a patient requiring cartilage regeneration by injection without a surgical operation, and due to the high possibility of differentiating into chondrocytes, particularly, hyaline chondrocytes, a cartilage regeneration effect is exhibited, indicating high industrial applicability.

The invention claimed is:

1. A method of preparing an injectable chondrocyte pellet comprising differentiated hyaline chondrocytes, the method comprising:

(a) culturing human induced pluripotent stem cells (hiPSCs) derived from cord blood mononuclear cells to form and obtain an embryoid body;
(b) inducing the embryoid body obtained in Step (a) into outgrowth cells and isolating the outgrowth cells;
(c) centrifuging 1,500 to 2,500 of the outgrowth cells isolated in Step (b) at a speed of 1,600 to 2,000 rpm to form a chondrocyte pellet; and
(d) culturing the chondrocyte pellet formed in step (c) in a serum-free medium comprising a human bone morphogenetic protein (BMP) and a transforming growth factor-beta (TGF-β), wherein the chondrocyte pellet in step (c) has a diameter of 200 to 300 μm.

2. The method of claim 1, wherein the culture in Step (a) is adherent culture.

3. The method of claim 1, wherein the induction in Step (b) is performed on a gelatin-coated plate.

4. A method of treating an arthritis, comprising:
administering the chondrocyte pellet prepared by the method of claim 1 to an arthritis patient via intra-articular injection.

5. The method of claim 4, wherein the administration is performed using a syringe.

6. The method of claim 4, wherein the arthritis is any one or more selected from osteoarthritis, rheumatoid arthritis, psoriatic arthritis, septic arthritis, osteochondritis dissecans, arthritis due to joint and ligament damage, and arthritis due to meniscus injury.

* * * * *